(12) United States Patent
Shenkal et al.

(10) Patent No.: US 10,588,344 B2
(45) Date of Patent: Mar. 17, 2020

(54) LOW EMISSIONS ELECTRONIC SMOKING DEVICE AND EMISSIONS FILTERING DEVICE

(71) Applicant: Philter Labs, Inc., Encinitas, CA (US)

(72) Inventors: Yuval Shenkal, Cardiff, CA (US); John Grimm, Santee, CA (US)

(73) Assignee: Philter Labs, Inc., San Diego, CA (US)

( * ) Notice: Subject to any disclaimer, the term of this patent is extended or adjusted under 35 U.S.C. 154(b) by 0 days.

(21) Appl. No.: 16/257,881

(22) Filed: Jan. 25, 2019

(65) Prior Publication Data

US 2019/0150516 A1 May 23, 2019

Related U.S. Application Data

(63) Continuation-in-part of application No. 15/884,082, filed on Jan. 30, 2018, now Pat. No. 10,470,498.

(60) Provisional application No. 62/452,871, filed on Jan. 31, 2017.

(51) Int. Cl.
| | | |
|---|---|---|
| A24F 7/04 | (2006.01) | |
| A24F 47/00 | (2020.01) | |
| A24F 3/00 | (2006.01) | |
| A24F 13/00 | (2006.01) | |
| B01D 39/16 | (2006.01) | |
| B01D 53/02 | (2006.01) | |
| B01D 46/00 | (2006.01) | |
| B01D 46/24 | (2006.01) | |
| A61L 9/014 | (2006.01) | |
| B01D 53/04 | (2006.01) | |

(52) U.S. Cl.
CPC .................. *A24F 7/04* (2013.01); *A24F 3/00* (2013.01); *A24F 13/00* (2013.01); *A24F 47/008* (2013.01); *A61L 9/014* (2013.01); *B01D 39/1692* (2013.01); *B01D 46/003* (2013.01); *B01D 46/0036* (2013.01); *B01D 46/0038* (2013.01); *B01D 46/2411* (2013.01); *B01D 53/02* (2013.01); *B01D 53/0407* (2013.01); *A61L 2209/13* (2013.01); *B01D 2239/045* (2013.01); *B01D 2253/102* (2013.01); *B01D 2257/80* (2013.01); *B01D 2257/90* (2013.01); *B01D 2259/4541* (2013.01)

(58) Field of Classification Search
CPC ....................................................... A24F 7/04
See application file for complete search history.

(56) References Cited

U.S. PATENT DOCUMENTS

| | | |
|---|---|---|
| 3,731,678 A | 5/1973 | Pyzel |
| 4,899,766 A | 2/1990 | Ross |
| 5,160,518 A | 11/1992 | Vega, Jr. |
| 5,353,814 A | 10/1994 | Martin |
| 5,396,907 A | 3/1995 | Rojas Henao et al. |
| 5,495,859 A | 3/1996 | Bowen et al. |
| 5,529,078 A | 6/1996 | Rehder |

(Continued)

*Primary Examiner* — James Harvey
(74) *Attorney, Agent, or Firm* — Sheppard, Mullin, Richter & Hampton LLP

(57) ABSTRACT

The present disclosure provides, in one embodiment, a filter device comprising a mouthpiece, a filter assembly in communication with the mouthpiece for filtering air exhaled into the mouthpiece, and an outlet check valve which permits air to be exhaled through the mouthpiece into the filter assembly, and substantially prohibits air from being inhaled from the filter assembly into the mouthpiece.

14 Claims, 26 Drawing Sheets

(56) References Cited

U.S. PATENT DOCUMENTS

| | | |
|---|---|---|
| 5,666,978 A | 9/1997 | Counts et al. |
| 5,814,118 A | 9/1998 | Wickland et al. |
| 6,761,169 B2 | 7/2004 | Eswarappa |
| 2006/0107965 A1 | 5/2006 | Marshall |
| 2008/0060664 A1 | 3/2008 | Richards |
| 2008/0149118 A1 | 6/2008 | Oglesby et al. |
| 2008/0230052 A1 | 9/2008 | Montaser |
| 2011/0073120 A1 | 3/2011 | Adamic |
| 2011/0277757 A1 | 11/2011 | Terry et al. |
| 2012/0325227 A1 | 12/2012 | Robinson |
| 2013/0255702 A1 | 10/2013 | Griffith |
| 2014/0123990 A1 | 5/2014 | Timmermans |
| 2014/0190496 A1 | 7/2014 | Wensley et al. |
| 2015/0150305 A1 | 6/2015 | Shenkal |
| 2015/0216236 A1 | 8/2015 | Bless et al. |
| 2015/0342259 A1 | 12/2015 | Baker |
| 2016/0219932 A1 | 8/2016 | Glaser |
| 2016/0270446 A1 | 9/2016 | Shenkal |
| 2017/0245545 A1 | 8/2017 | Johnson, III et al. |
| 2018/0060664 A1 | 3/2018 | Richards |
| 2019/0037923 A1* | 2/2019 | Shenkal .................... A24F 3/00 |
| 2019/0150516 A1* | 5/2019 | Shenkal ................ A24F 47/008 |

* cited by examiner

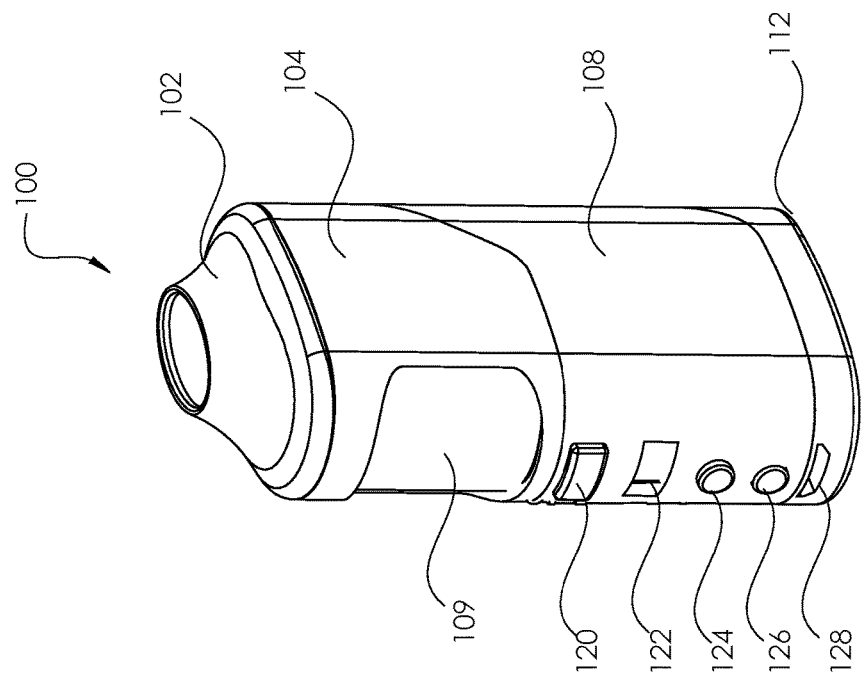
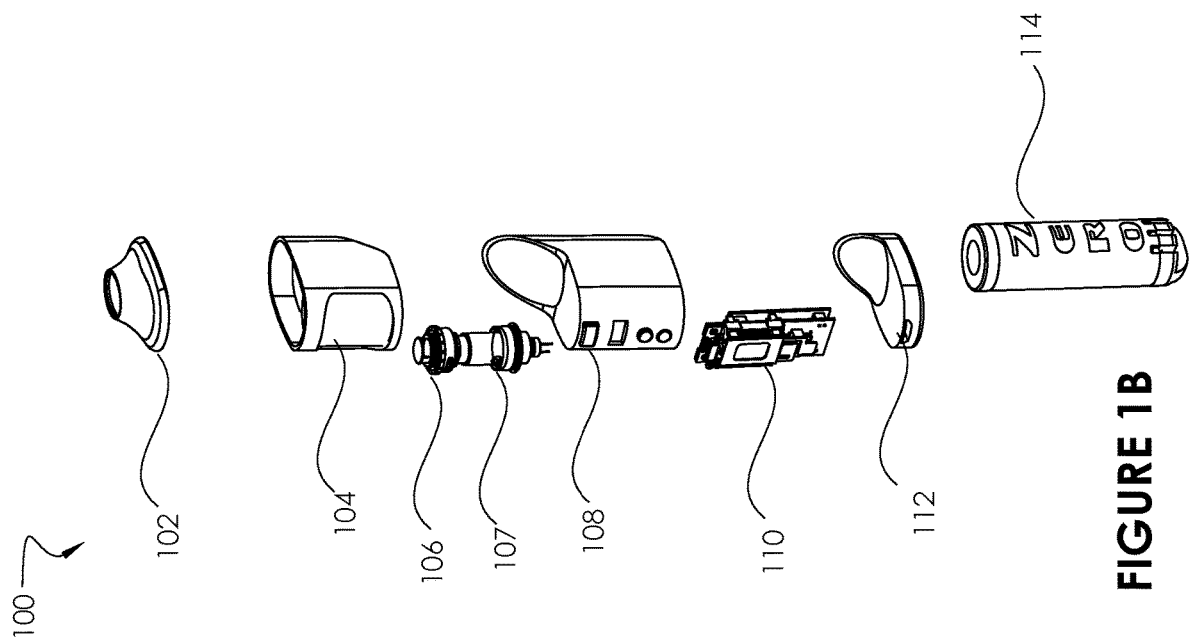

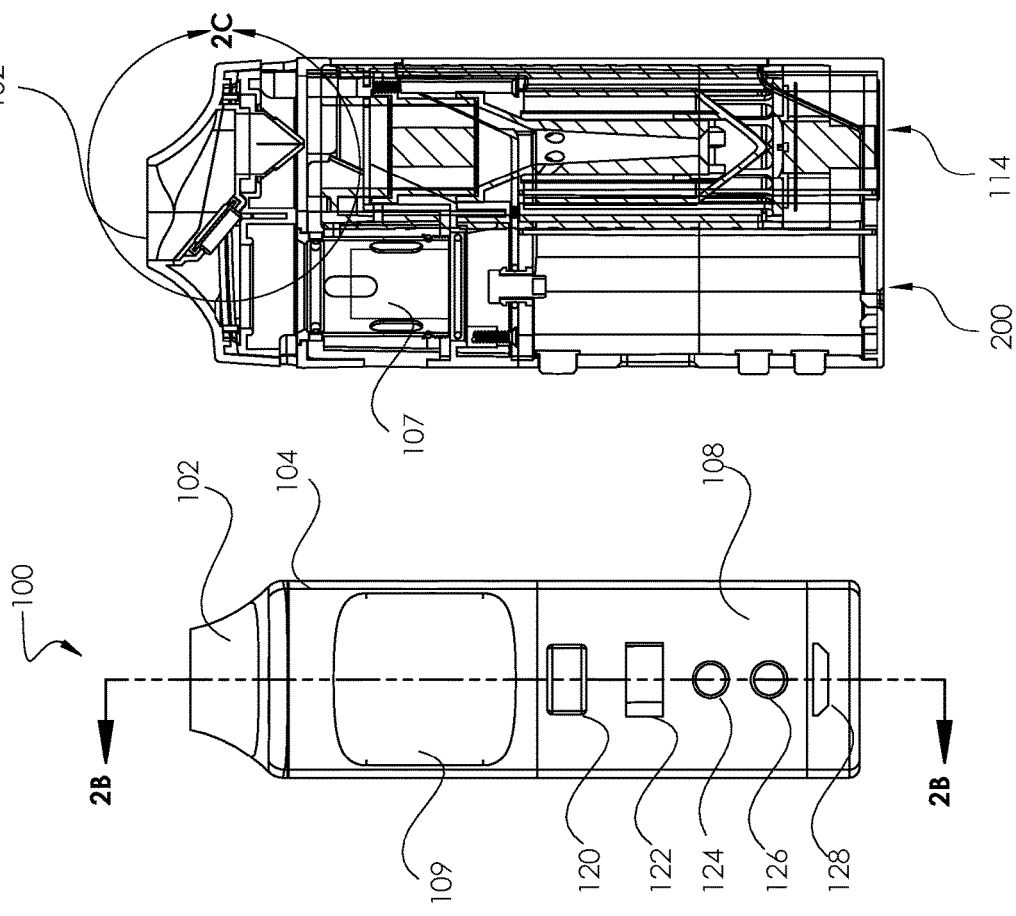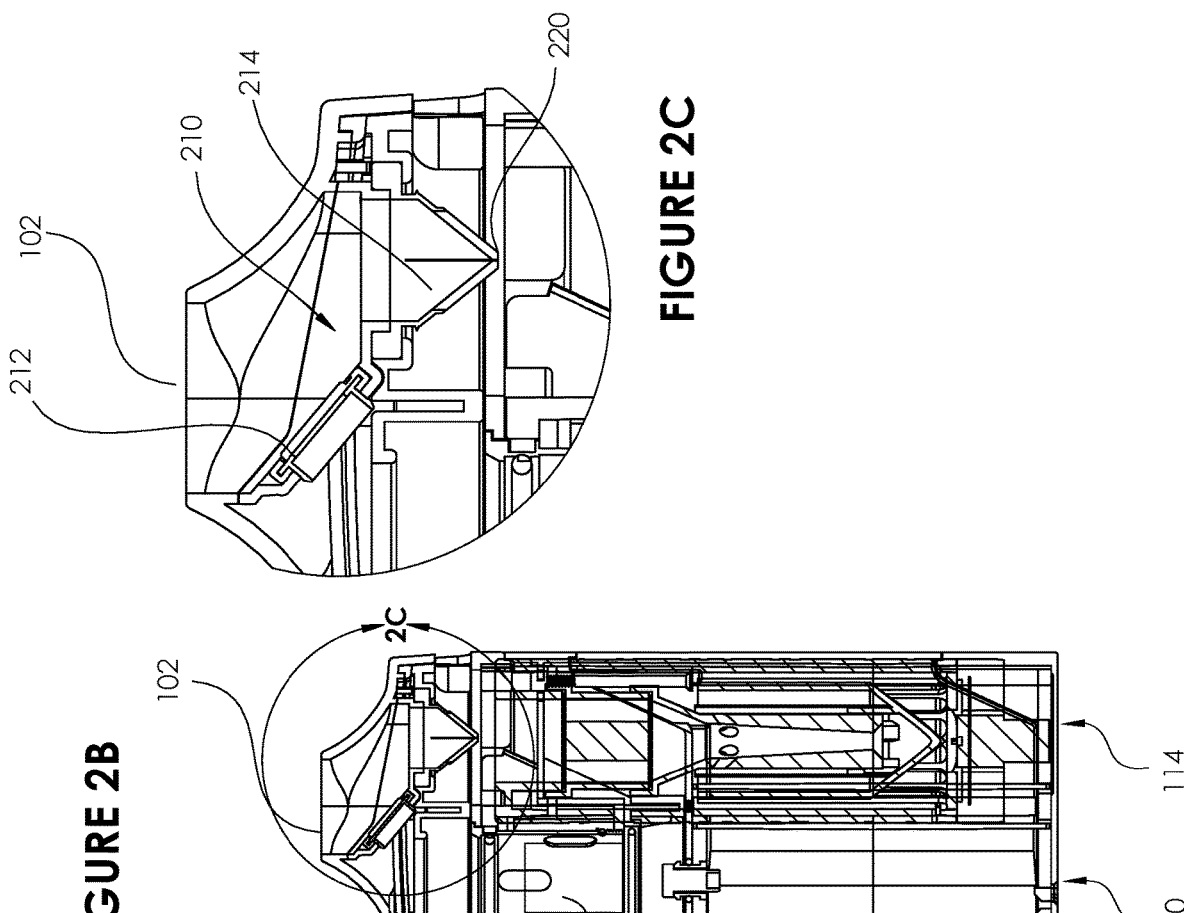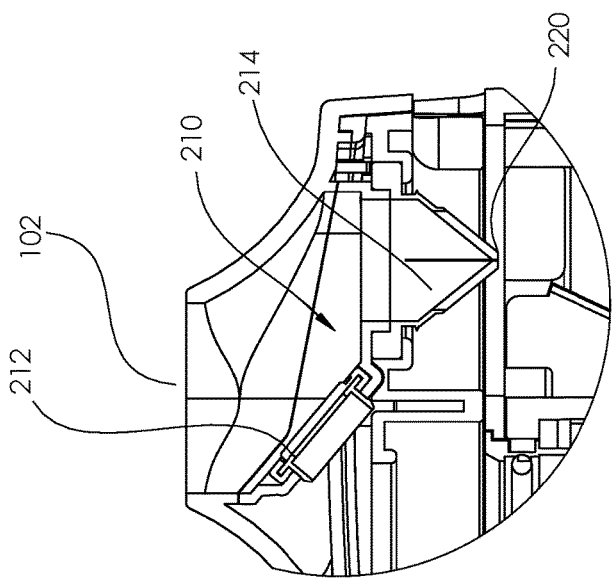

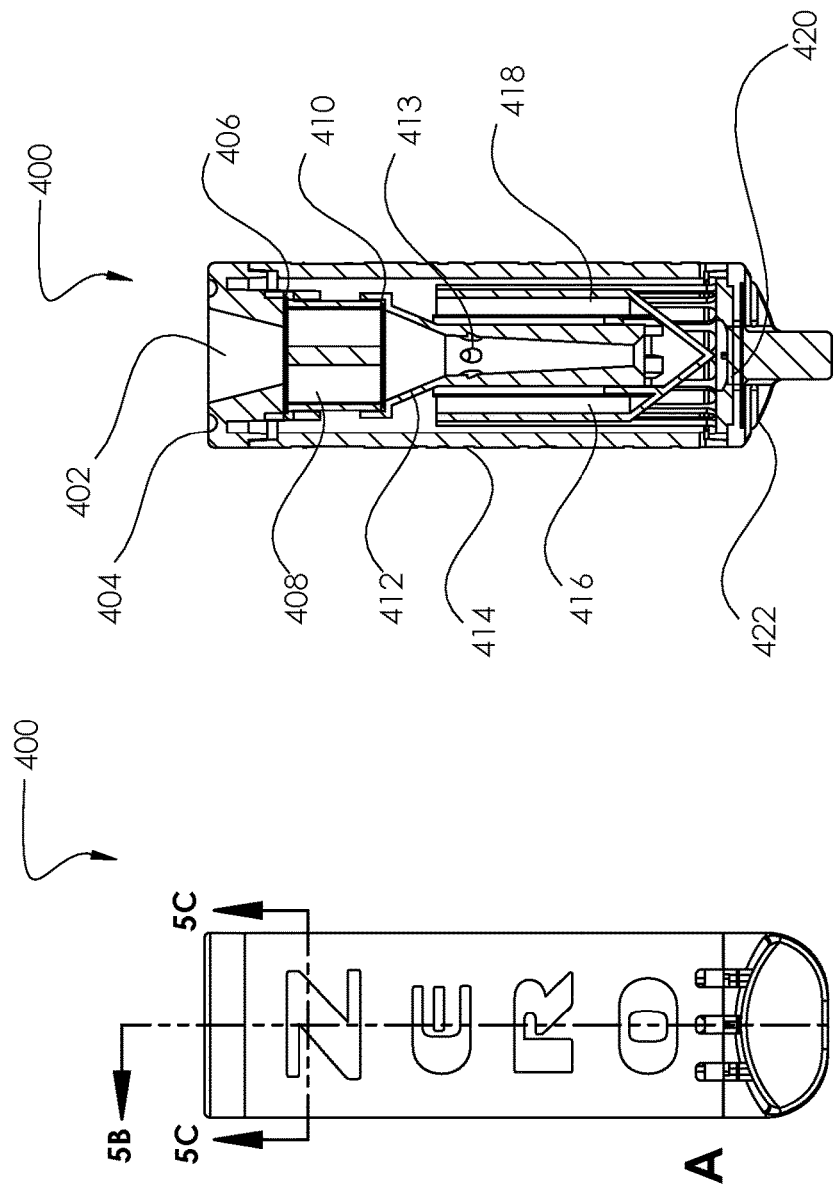
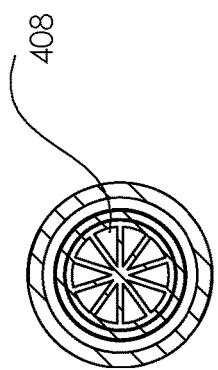
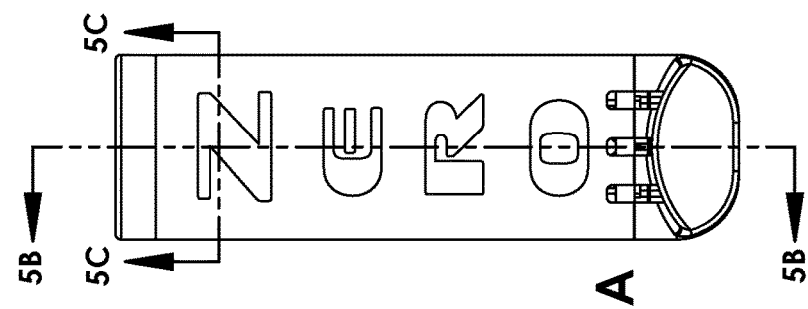
FIGURE 5B
FIGURE 5C
FIGURE 5A

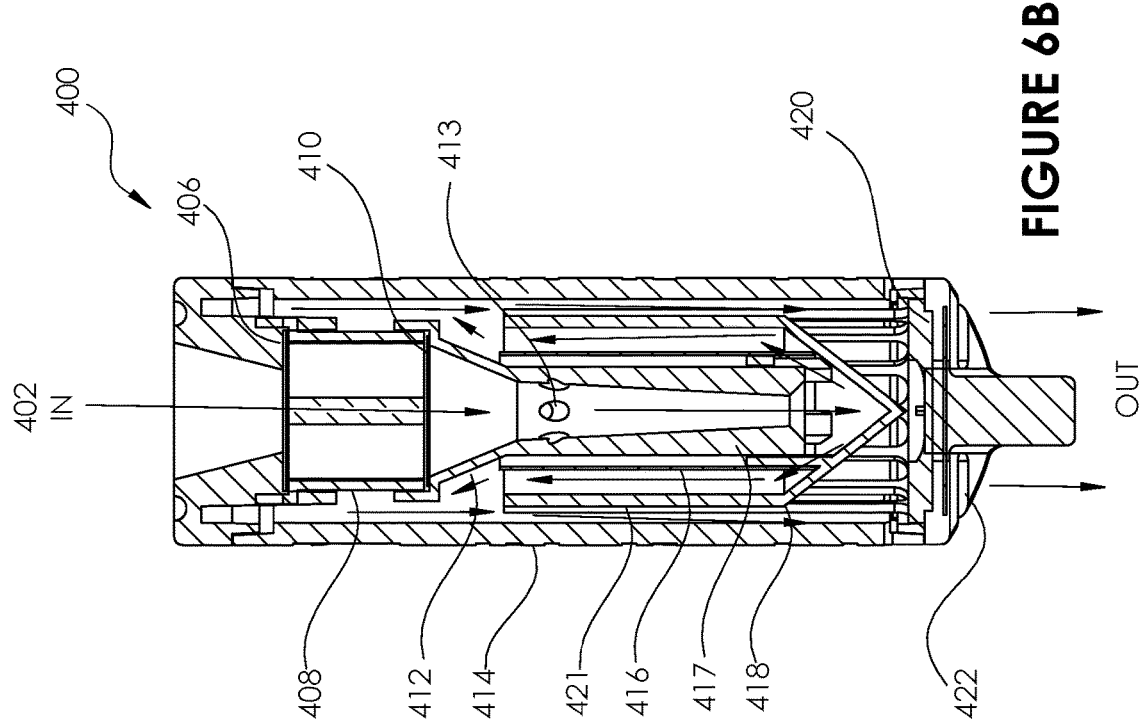
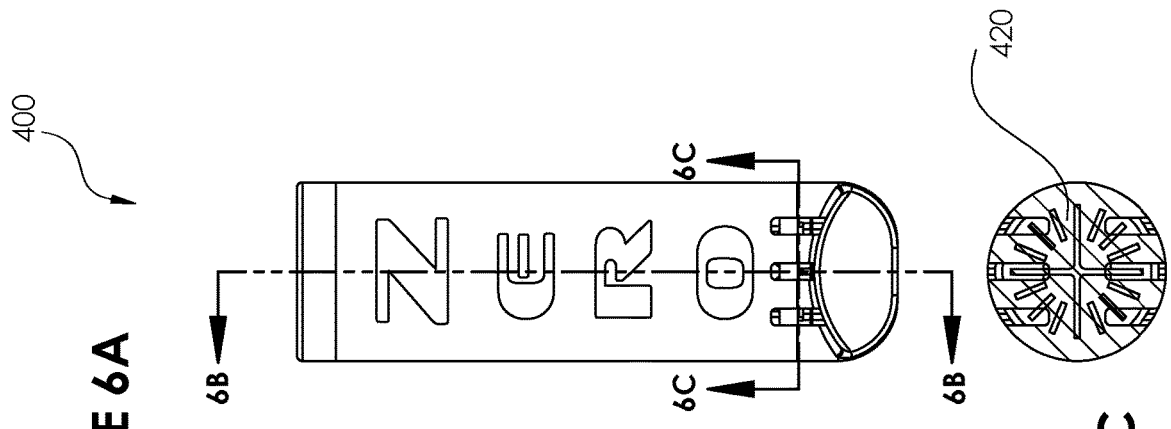

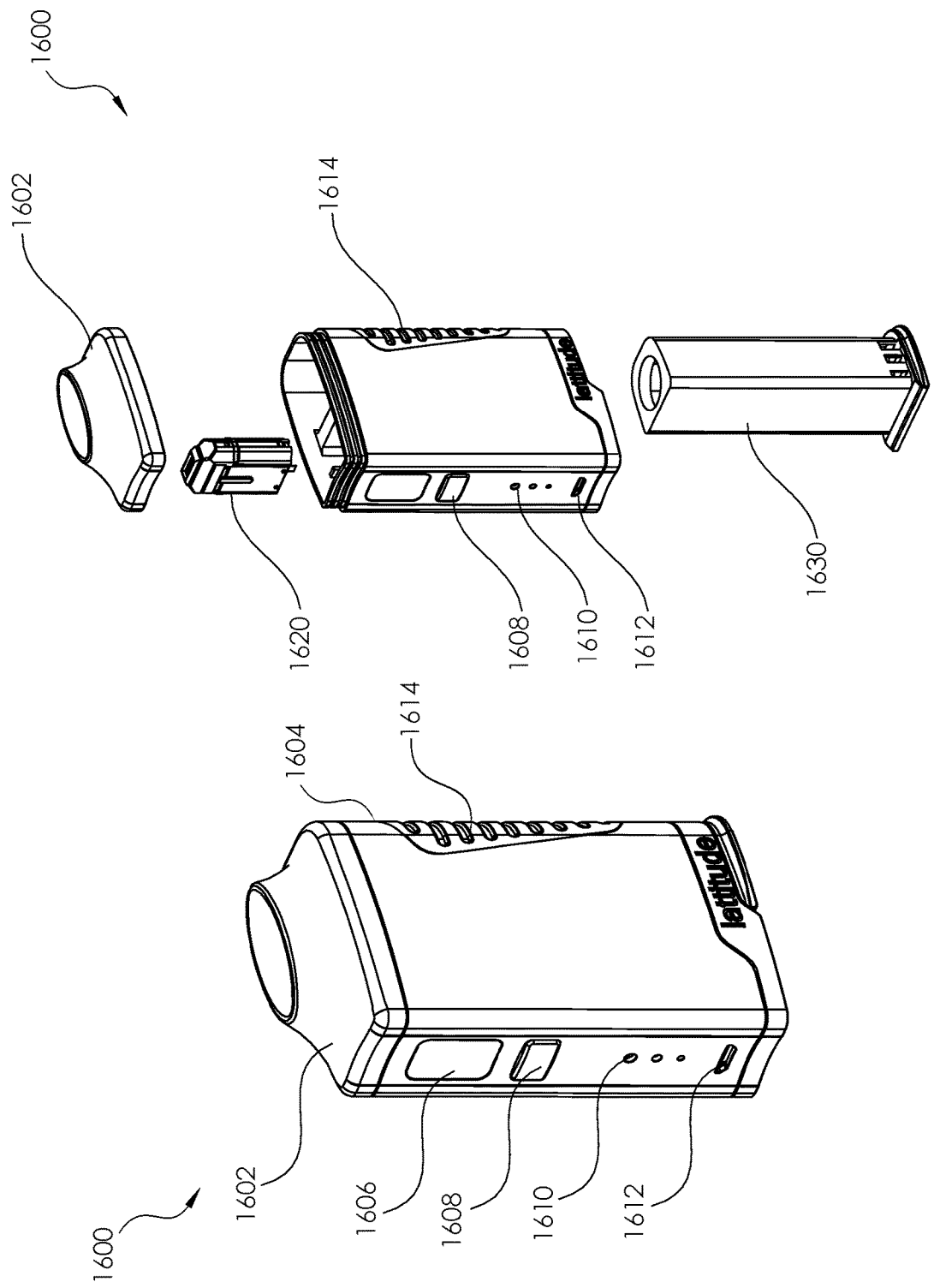

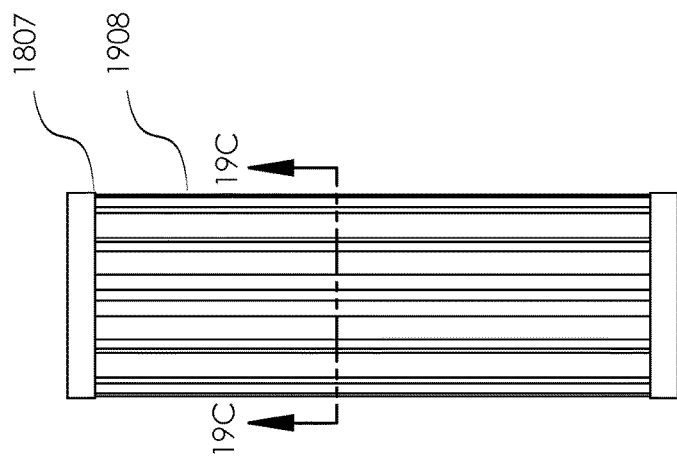
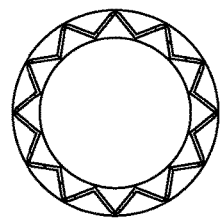
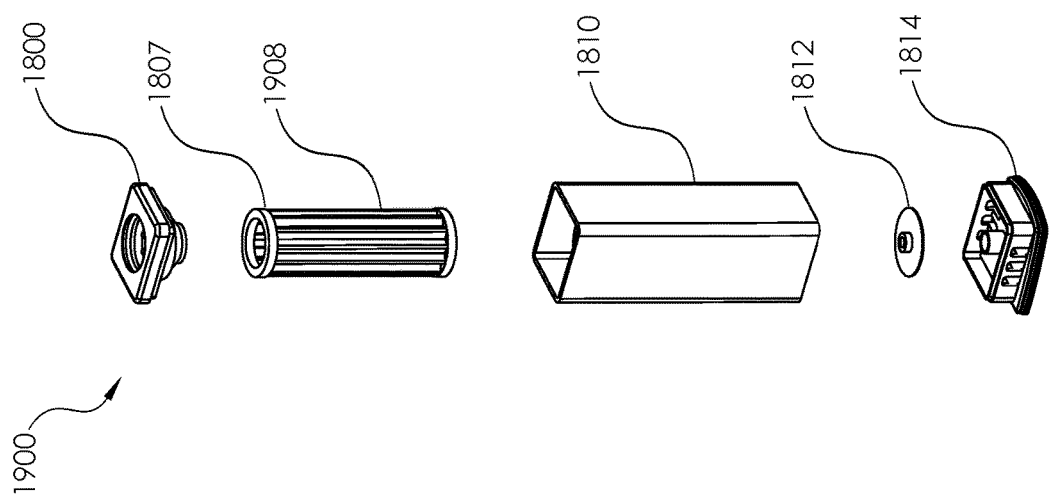
FIGURE 19B
FIGURE 19C
FIGURE 19A

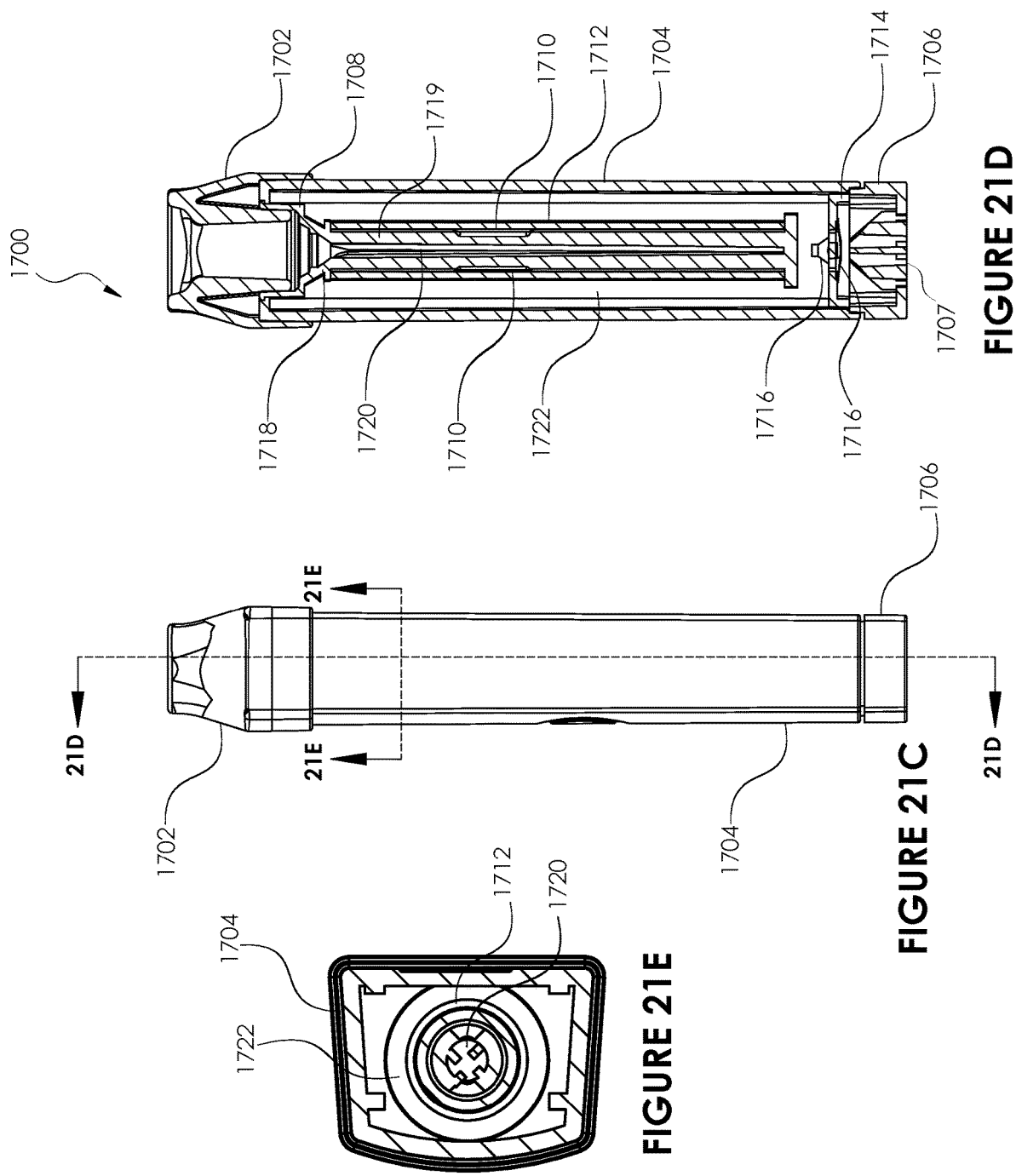

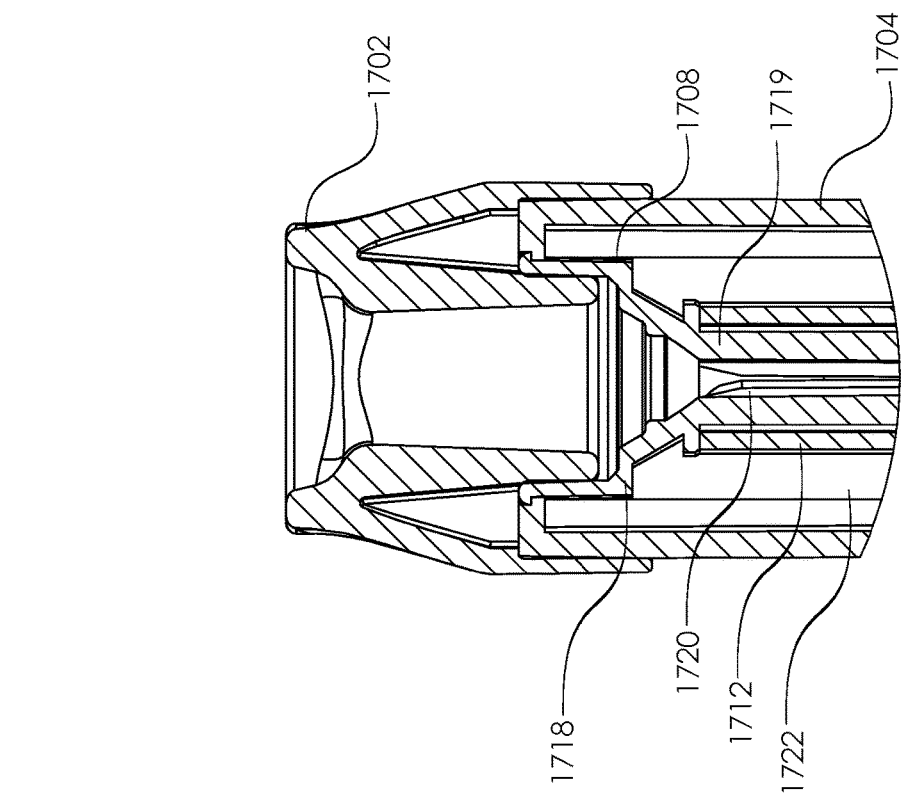
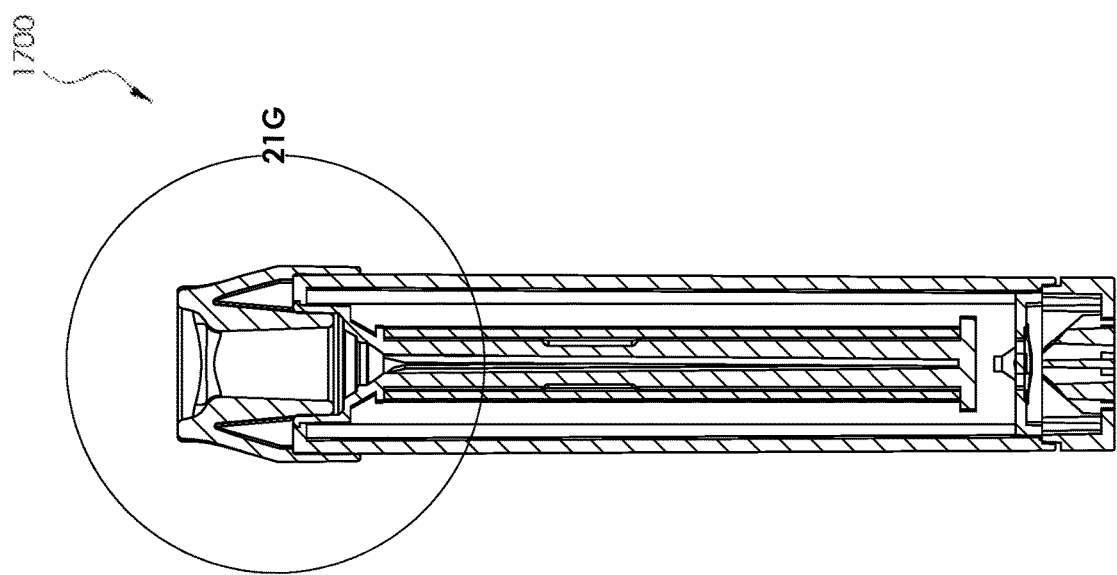
FIGURE 21G
FIGURE 21F

LOW EMISSIONS ELECTRONIC SMOKING DEVICE AND EMISSIONS FILTERING DEVICE

CROSS-REFERENCE TO RELATED APPLICATIONS

This application is a continuation-in-part of U.S. patent application Ser. No. 15/884,082, filed Jan. 30, 2018, and entitled "LOW EMISSIONS ELECTRONIC SMOKING DEVICE," which claims priority to U.S. Provisional Application No. 62/452,871, filed Jan. 31, 2017 and entitled "LOW EMISSIONS ELECTRONIC SMOKING DEVICE," the entire contents of which are hereby incorporated by reference in their entirety as if fully set forth herein.

FIELD OF THE INVENTION

The present technology relates to the field of electronic smoking devices. More particularly, the present technology relates to a low emissions electronic smoking device.

BACKGROUND

Smoking plant material has been practiced in numerous cultures for many centuries. However, as scientific and medical evidence has mounted regarding the environmental and health risks of smoking emissions (e.g., second-hand smoke), traditional smoking of tobacco or other plant-based materials has been banned in many public spaces. Furthermore, social norms have generally come to discourage smoking in any venue in which others may be affected by smoking emissions.

Electronic smoking devices, commonly known as e-cigarettes, vaporizers, or vapes, have grown in popularity to replace or supplement traditional smoking mediums, such as cigarettes or pipes. Electronic smoking devices have generally been purported to be healthier than, for example, traditional cigarettes. Electronic smoking devices have also generally been purported to have fewer harmful emissions than traditional smoking mediums. However, electronic smoking devices do still cause emissions, which may potentially pose a health and/or environmental risk, and may be viewed negatively in a public or social environment.

SUMMARY OF THE INVENTION

In one embodiment, the present disclosure can be embodied in a filter device comprising a mouthpiece, a filter assembly in communication with the mouthpiece for filtering air exhaled into the mouthpiece, and an outlet check valve which permits air to be exhaled through the mouthpiece into the filter assembly, and substantially prohibits air from being inhaled from the filter assembly into the mouthpiece.

In an embodiment, the outlet check valve is a one-way valve which opens when a user exhales into the mouthpiece, and seals when a user inhales from the mouthpiece.

In an embodiment, the mouthpiece is removably secured to the filter assembly.

In an embodiment, the filter assembly comprises a venturi core. The venturi core comprises a funneled inlet portion having a wide end directed towards the mouthpiece to receive emissions blown into the mouthpiece and a narrow end directed away from the mouth piece, and a stem portion extending from the narrow end of the funneled inlet portion.

In an embodiment, an inner surface of the stem portion defines an inner cavity, and the inner surface of the stem portion comprises a plurality of walls.

In an embodiment, the stem portion comprises one or more openings to permit emissions to exit the inner cavity.

In an embodiment, the one or more openings are covered by a filter.

In an embodiment, the filter is a HEPA filter.

In an embodiment, the filter is a polyester HEPA filter.

In an embodiment, the stem portion is housed within an outer body, an area between the stem portion and the outer body defines an outer cavity, and the one or more openings permit emissions to exit the inner cavity into the outer cavity.

In an embodiment, the outer cavity houses a plurality of odor-absorbing pellets.

In an embodiment, the plurality of odor-absorbing pellets comprise a plurality of carbon pellets.

In an embodiment, the outer cavity houses a plurality of moisture-absorbing pellets.

In an embodiment, the outer body is hollow and has a first open end opposite a second open end, and the outer body is sealed at the first open end by the funneled inlet portion of the venturi core, and the outer body is secured at the second end to a base enclosure. The base enclosure comprises one or more openings, and the outlet check valve is configured to selectively seal the one or more openings based on a direction of air flow through the filter assembly.

In an embodiment, the outlet check valve is configured to be pushed away from the one or more openings in the base enclosure when a user exhales into the mouthpiece, and configured to be pulled towards the one or more openings in the base enclosure, sealing the one or more openings, when a user inhales into the mouthpiece.

The present disclosure may also be embodied in one or more methods for using, assembling, and/or making the various electronic smoking devices, filter cartridge assemblies, and standalone filter devices described herein.

Other features and advantages of the invention should become apparent from the following description of the preferred embodiments, taken in conjunction with the accompanying drawings, which illustrate, by way of example, the principles of the invention.

BRIEF DESCRIPTION OF THE DRAWINGS

FIG. 1A illustrates a perspective view of an electronic smoking device, according to an embodiment of the present disclosure.

FIG. 1B illustrates an exploded view of the electronic smoking device of FIG. 1A, according to an embodiment of the present disclosure.

FIG. 2A illustrates a front plan view of the electronic smoking device of FIG. 1A, according to an embodiment of the present disclosure.

FIG. 2B illustrates a cross-sectional view of the electronic smoking device of FIG. 2A taken along line 2B-2B of FIG. 2A, according to an embodiment of the present disclosure.

FIG. 2C illustrates a close-up view of the cross-sectional view shown in FIG. 2B defined by the area 2C of FIG. 2B, according to an embodiment of the present disclosure.

FIG. 5A illustrates a plan view of the filter cartridge assembly of FIG. 4, according to an embodiment of the present disclosure.

FIG. 5B illustrates a cross-sectional view of the filter cartridge assembly of FIG. 5A taken along line 5B-5B of FIG. 5A, according to an embodiment of the present disclosure.

FIG. 5C illustrates a cross-sectional view of the filter cartridge assembly of FIG. 5A taken along line 5C-5C of FIG. 5A, according to an embodiment of the present disclosure.

FIG. 6A illustrates a plan view of the filter cartridge assembly of FIG. 4, according to an embodiment of the present disclosure.

FIG. 6B illustrates a cross-sectional view of the filter cartridge assembly of FIG. 6A taken along line 6B-6B of FIG. 6A, according to an embodiment of the present disclosure.

FIG. 6C illustrates a cross-sectional view of the filter cartridge assembly of FIG. 6A taken along line 6C-6C of FIG. 6A, according to an embodiment of the present disclosure.

FIG. 16A illustrates a perspective view of an electronic smoking device, according to an embodiment of the present disclosure.

FIG. 16B illustrates an exploded view of the electronic smoking device of FIG. 16A, according to an embodiment of the present disclosure.

FIG. 19A illustrates an exploded view of a filter cartridge assembly, according to an embodiment of the present disclosure.

FIG. 19B illustrates a plan view of a mesh filter structure, according to an embodiment of the present disclosure.

FIG. 19C illustrates a cross-sectional view of the mesh filter structure of FIG. 19B taken along the line 19C-19C of FIG. 19B, according to an embodiment of the present disclosure.

FIG. 21C illustrates a side plan view of the filter device of FIG. 21A, according to an embodiment of the present disclosure.

FIG. 21D illustrates a cross-sectional view of the filter device of FIG. 21C taken along the line 21D-21D of FIG. 21C, according to an embodiment of the present disclosure.

FIG. 21E illustrates a cross-sectional view of the filter device of FIG. 21C taken along the line 21E-21E of FIG. 21C, according to an embodiment of the present disclosure.

FIG. 21F illustrates the cross-sectional view of the filter device previously depicted in FIG. 21D, according to an embodiment of the present disclosure.

FIG. 21G illustrates a close-up view of the filter device of FIG. 21F, according to an embodiment of the present disclosure.

Figure 3C:
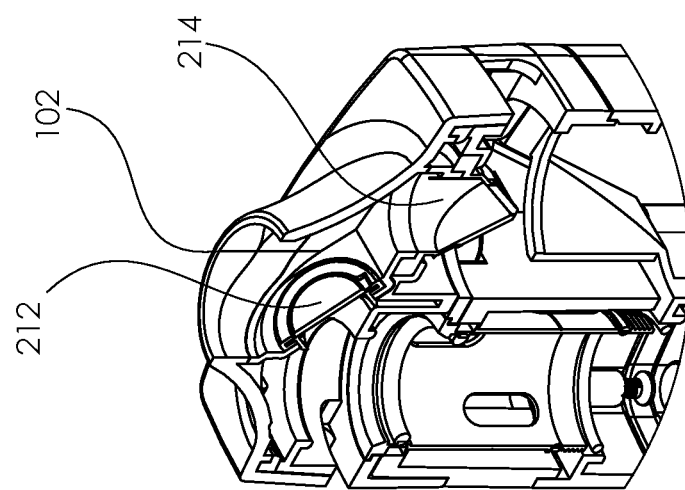
FIGS. 3A-C illustrate various cross-sectional views of a mouthpiece and diverter valve, according to an embodiment of the present disclosure.

The figures depict various embodiments of the disclosed technology for purposes of illustration only, wherein the figures use like reference numerals to identify like elements. One skilled in the art will readily recognize from the following discussion that alternative embodiments of the structures and methods illustrated in the figures can be employed without departing from the principles of the disclosed technology described herein.

DETAILED DESCRIPTION

Low Emissions Electronic Smoking Device

Smoking plant material has been practiced in numerous cultures for many centuries. However, as scientific and medical evidence has mounted regarding the environmental and health risks of smoking emissions (e.g., second-hand smoke), traditional smoking of tobacco or other plant-based materials has been banned in many public spaces. Furthermore, social norms have generally come to discourage smoking in any venue in which others may be affected by smoking emissions.

Electronic smoking devices, commonly known as e-cigarettes, vaporizers, or vapes, have grown in popularity to replace or supplement traditional smoking mediums, such as cigarettes or pipes. Electronic smoking devices have generally been purported to be healthier than, for example, traditional cigarettes. Electronic smoking devices have also generally been purported to have fewer harmful emissions than traditional smoking mediums. However, electronic smoking devices do still cause emissions, which may potentially pose a health and/or environmental risk, and may be viewed negatively in a public or social environment.

Therefore, a need exists for an electronic smoking device that reduces, minimizes, and/or altogether eliminates harmful or undesirable emissions. Previous works by the inventors of the present disclosure have presented improvements for addressing some of the problems discussed above. These works include U.S. Pat. No. 9,402,422 to Shenkal, filed Nov. 3, 2014, issued Aug. 2, 2016, and entitled "Hybrid E-Cigarette/Vaporizer with Exhale Filter Capability," and U.S. patent application Ser. No. 15/070,186 to Shenkal et al., filed Mar. 15, 2016, entitled "E-Cigarette With Valve Allowing Exhale Filter," the entire contents of which are hereby incorporated by reference as if fully set forth herein. The present disclosure provides for additional variations and improvements on low emissions (or zero emissions) electronic smoking devices capable of filtering smoking emissions.

FIG. 1A illustrates a perspective view of an electronic smoking device 100, according to an embodiment of the present disclosure. FIG. 1B illustrates an exploded view of the electronic smoking device 100, according to an embodiment of the present disclosure. The electronic smoking device 100 includes a mouthpiece 102 secured to a mid-enclosure 104. In the example embodiment shown, the mouthpiece 102 has a curved design that is designed to ergonomically seal against a user's mouth while allowing for maximum inhale and/or exhale. In certain embodiments, the mouthpiece 102 can be a disposable and/or replaceable component. Further, in various embodiments, the mouthpiece 102 can be imbued with various flavors and/or scents (e.g., by impregnating the material of the mouthpiece 102). The mid-enclosure 104 houses a cooker chamber 107. The cooker chamber 107 is configured to contain a material to be heated and vaporized, such as liquid, oil, flower, or leaf material. The cooker chamber 107 can comprise a transparent material (such as glass or clear plastic), and the mid-enclosure 104 can include a transparent portion 109 (or a cut-out portion) so that a user can view the material contained within the cooker chamber 107.

The cooker chamber 107 includes a coil 106 to heat material contained within the cooker chamber 107. The coil 106 is in electronic communication with a printed circuit board (PCB)/battery 110, which is housed within an electronics housing 108. The PCB/battery 110 provides electrical power to the coil 106 to heat the coil 106, and also has circuitry to control various functions of the electronic smoking device 100. These functions may be controlled by a user using various inputs provided on the electronics housing 108. For example, the electronics housing 108 has an igniter button 120, which causes power to be transmitted to the coil 106, thereby heating the coil 106 and vaporizing the material contained in the cooker chamber 107. The electronics housing 108 also includes a display 122 for displaying information, such as a current wattage or charge level of the electronic smoking device 100. The electronics housing 108 includes buttons 124, 126 for selecting various options. For example, the buttons 124, 126 can be used to set a wattage for the electronic smoking device 100. The electronics housing 108 also includes a micro-USB charging port 128 for charging the PCB/battery 110. A bottom cover 112 encloses the PCB/battery 110 within the electronics housing 108.

The electronic smoking device 100 comprises a vaporizer portion, which, in one embodiment, comprises the cooker chamber 107, the coil 106, the electronics housing 108, and the PCB/battery 110. The vaporizer portion allows a user to heat and inhale vaporized material. The electronic smoking device 100 also includes a filter portion, which comprises a filter cartridge assembly 114. The filter cartridge assembly 114 allows a user to exhale emissions back into the electronic smoking device 100 to filter out odors and/or particulate matter in the emissions. As such the vaporizer portion can be considered to provide an "inhale" function of the electronic smoking device 100, while the filter cartridge assembly 114 and/or the filter portion can be considered to provide an "exhale" function of the electronic smoking device 100. As will be described in greater detail below, a user can both inhale vaporized material and exhale emissions via the mouthpiece 102.

As can be seen in FIG. 1B, and described in greater detail herein, the filter cartridge assembly 114 can be secured to the mouthpiece 102 by inserting the filter cartridge assembly 114 through the bottom cover 112, the electronics housing 108, and the mid enclosure 104. In the depicted embodiment, the filter cartridge assembly 114 is inserted into and/or removed from the electronic smoking device 100 through the bottom of the electronic smoking device 100. In certain embodiments, the filter cartridge assembly 114 may be disposable and/or replaceable, such that when a filter cartridge assembly 114 is no longer effective or less effective (e.g., due to overuse), it can be replaced with a new one.

FIG. 2A illustrates a front plan view of the electronic smoking device 100. FIG. 2B illustrates a cross-sectional view of the electronic smoking device 100 of FIG. 2A taken along line 2B-2B of FIG. 2A, according to an embodiment of the present disclosure. In FIG. 2B, it can be seen that the filter portion comprising the filter cartridge assembly 114 occupies one side of the electronic smoking device 100, and the vaporizer portion 200 occupies the other side of the electronic smoking device 100. When a user inhales on the mouthpiece 102, vaporized material is pulled up into the user's mouth from the cooker chamber 107. When a user exhales into the mouthpiece 102, emissions from the user's mouth are directed into the filter cartridge assembly 114. As the emissions work through the various filtration mechanisms contained in the filter cartridge assembly 114 (various embodiments of which will be described in greater detail herein), odors and/or particulate matter are filtered out. Filtered emissions which are substantially free of odors and/or particular matter are then expelled out of the bottom of the filter cartridge assembly 114.

It can be appreciated that using a single mouthpiece for both inhalation of vaporized material and exhalation of emissions can pose various challenges. For example, when a user inhales, only vaporized material from the cooker chamber 107 should be pulled up through the mouthpiece 102. The user should not be exposed to emissions that have been previously blown into the filter cartridge assembly 114. Similarly, when a user exhales, the user's exhaled emissions should be diverted to the filter cartridge assembly 114, and such emissions should not enter the cooker chamber 107. Furthermore, emissions diverted to the filter cartridge assembly 114 should pass through the filter cartridge assembly 114 with little to no leakage of unfiltered emissions, as leakage of unfiltered emissions would be contrary to the low emissions/zero emissions goal of the present disclosure.

In order to carry out these functions, in the embodiment shown in FIGS. 2A-2C, a diverter valve 210 is utilized to ensure that only vaporized material is inhaled by the user, and that exhaled emissions are correctly and effectively routed into the filter cartridge assembly 114. FIG. 2C illustrates a close-up view of the cross-sectional view shown in FIG. 2B defined by the area 2C-2C of FIG. 2B. FIG. 2C provides a close-up view of the diverter valve 210. The diverter valve 210 is sealed against the mouthpiece 102 so as to prevent any undesirable leakage of emissions from the filter cartridge assembly 114 and/or vaporized material from the cooker chamber 107. In certain embodiments, the diverter valve 210 includes two one-way valves: an inlet check valve 212 and an outlet check valve 214. The inlet check valve 212 is a one way valve that allows vapors to escape the cooker chamber into the mouthpiece 102 on inhale, but substantially blocks and/or prohibits emissions from entering the cooker chamber from the mouthpiece 102 on exhale. The outlet check valve 214 is a one way valve that allows exhaled emissions to enter from the mouthpiece 102 into the filter cartridge assembly 114, but substantially blocks and/or prohibits emissions from exiting the filter cartridge assembly 114 into the mouthpiece 102 on inhale.

In the depicted embodiment, the inlet check valve 212 is implemented using a one-way umbrella valve. When a user inhales on the mouthpiece 102, the pressure differential caused by the inhalation causes a body portion of the umbrella valve to lift away from a base portion, thereby allowing vaporized materials to move from the cooker chamber 107 into and out of the mouthpiece 102. However, when a user exhales into the mouthpiece 102, the body portion of the umbrella valve is pushed into the base portion. This causes the body portion to become seated within the base portion and closes the inlet check valve 212, thereby preventing any emissions from entering the cooker chamber 107 from the mouthpiece 102.

In the depicted embodiment, the outlet check valve 214 is implemented using a duckbill valve. The duckbill valve includes two or more flaps that meet at a point (220). When a user inhales on the mouthpiece 102, the flaps are pulled towards one another, thereby closing the outlet check valve 214. As such, inhalation will not cause any emissions to escape from the filter cartridge assembly 114 into the mouthpiece 102. When the user exhales into the mouthpiece 102, the flaps are pushed apart, creating an opening at the end point 220 and allowing exhaled emissions to flow from the mouthpiece 102 through the outlet check valve 214 into the filter cartridge assembly 114.

Although the example embodiments and figures depict the inlet check valve 212 as an umbrella valve, and the outlet check valve 214 as a duckbill valve, it should be understood that, in various embodiments, both the inlet check valve 212 and the outlet check valve 214 can be implemented using any one-way valve.

It can be seen in FIG. 2C that the inlet check valve 212 is tilted towards the outlet check valve 214. This angling of the inlet check valve 212 allows for any non-gaseous emissions (e.g., spit, resins, etc.) to be pulled towards the outlet check valve 214 and into the filter cartridge assembly 114 by gravitational forces. In certain scenarios, if the inlet check valve 212 is not angled towards the outlet check valve 214, liquids and sticky resins can become trapped within the mouthpiece 102, which can cause undesirable buildup of waste materials within the mouthpiece 102.

Figure 3A:
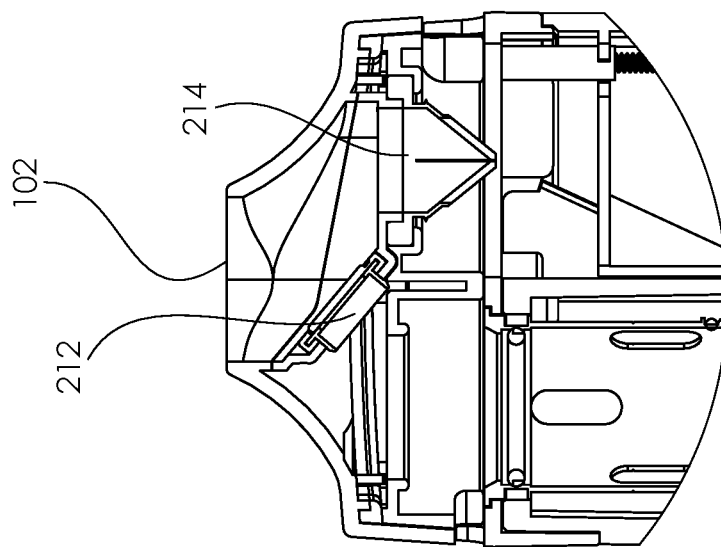
Figure 3B:
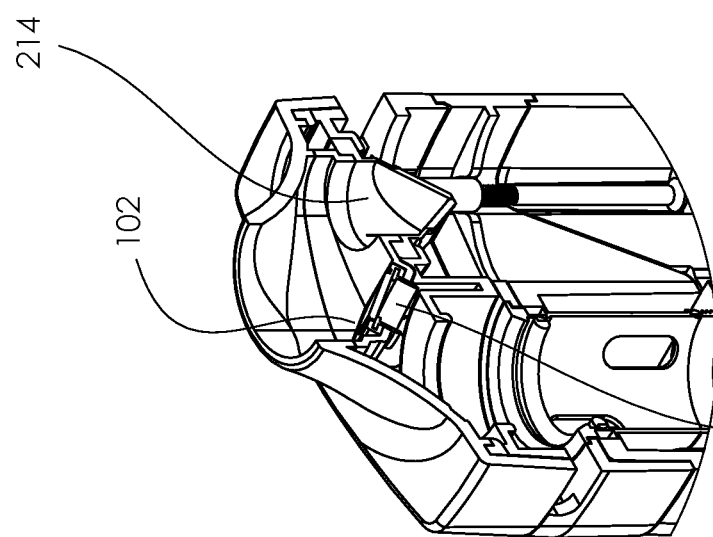

FIGS. 3A-C provide various cross-sectional views of the mouthpiece 102, the inlet check valve 212, and the outlet check valve 214.

Figure 4:
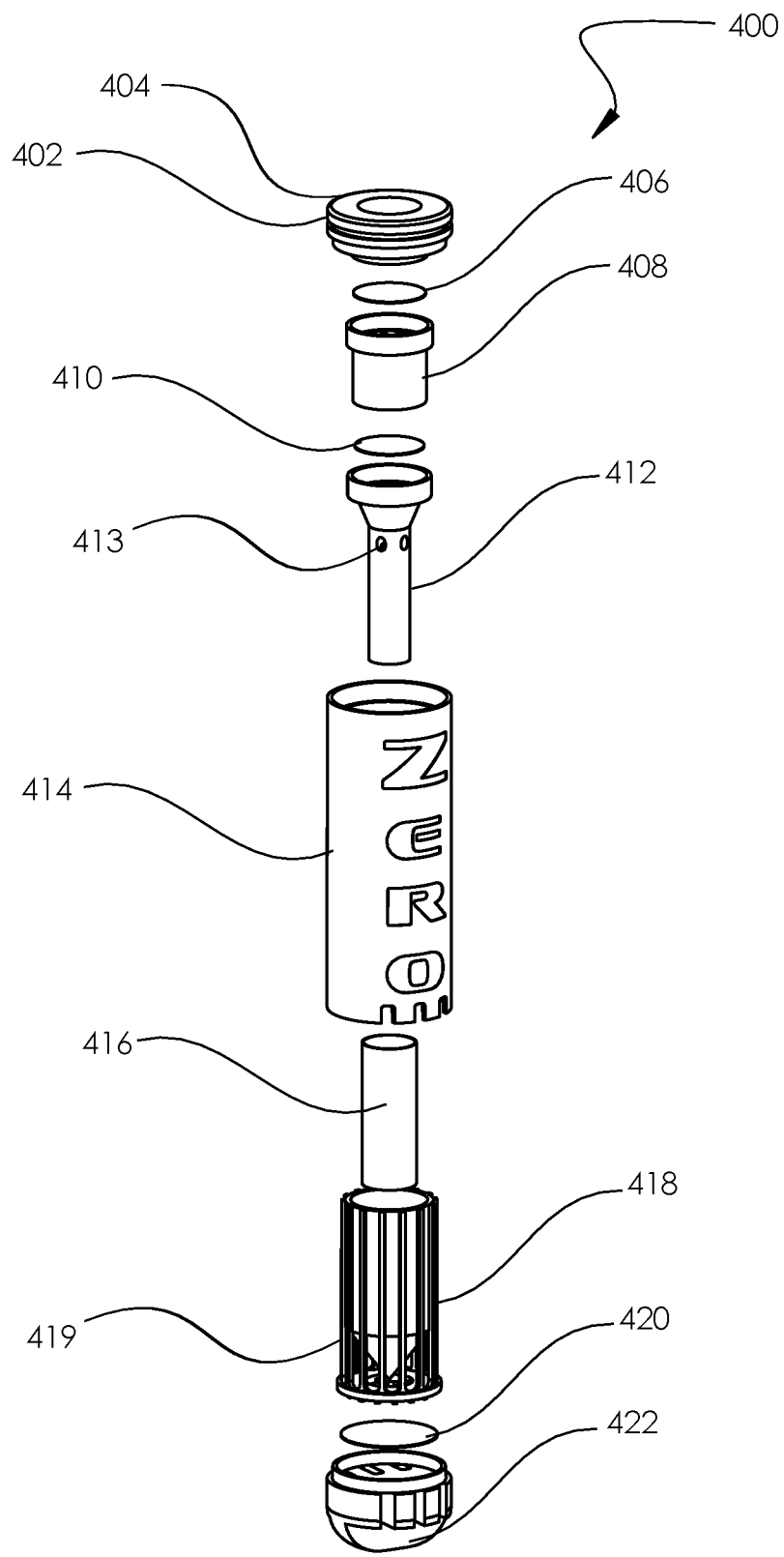
FIG. 4 illustrates an exploded view of a filter cartridge assembly, according to an embodiment of the present disclosure.

FIG. 4 illustrates an exploded view of an example filter cartridge assembly 400, in accordance with an embodiment of the present disclosure. In certain embodiments, the filter cartridge assembly 400 of FIG. 4 can be used as the filter cartridge assembly 114 of FIG. 1B.

The filter cartridge assembly 400 includes an open-ended tubular, cylindrical main enclosure body 414, which is at least partially enclosed at the top by an inlet cap 402 and at least partially enclosed at the bottom by a vented outlet cap 422. Between the inlet cap 402 and the vented outlet cap 422, and housed within the main enclosure body 414, are various filtering mechanisms that assist in removing odors and particulate matter from emissions blown into the filter cartridge assembly 400. Emissions are received into the filter cartridge assembly 400 via the inlet cap 402. Once the emissions pass through various filtering mechanisms housed within the main enclosure body 414, clean, filtered emissions are emitted via the vented outlet cap 422.

The inlet cap 402 can be configured to form an airtight seal with the outlet check valve 214 (see FIGS. 2B, 2C, 3A, 3B, 3C) to ensure that emissions that have entered the filter cartridge assembly 400 do not leak at the inlet cap/outlet check valve juncture. For example the inlet cap 402 can include threads that can be secured to corresponding threads surrounding the outlet check valve 214. The inlet cap 402 can also include an O-ring 404 to further ensure a tight seal between the inlet cap 402 and the outlet check valve 214.

Below the inlet cap 402 is a mesh screen 406. The mesh screen 406 acts as a demister and assists in condensing vapor emissions into condensate. The mesh screen 406, and any other components described herein, can be made from any appropriate materials. For example, in certain embodiments, the mesh screen 406 can be made of stainless steel or plastic. Below the mesh screen 406 is an air separator inlet 408. The mesh screen 406 can be sized to substantially cover a top opening of the air separator inlet 408. The air separator inlet 408 is an elongated tube that is divided into sections by partition walls that run through substantially the length of the air separator inlet 408. The partition walls are more clearly shown in FIG. 5C. The partition walls within the air separator inlet 408 divide exhaled emissions into various sections, and provide surface area that encourages further condensation of the emissions. The air separator inlet 408 feeds into a venturi reaction chamber 412. Positioned between the air separator inlet 408 and the venturi reaction chamber 412 is a polyester felt filter 410. The polyester felt filter 410 absorbs some portion of the condensate that has already formed, and also filters out some particulate matter in the emissions. In certain embodiments, the polyester felt filter 410 is a 1 micron polyester felt filter.

Emissions then enter the venturi reaction chamber 412, which is a funnel-shaped tube having a wider mouth portion that narrows into a narrower stem portion. This narrowing causes the emissions to accelerate through the venturi reaction chamber 412. As emissions accelerate through the venturi reaction chamber 412, additional air is pulled into the venturi reaction chamber 412 through openings 413 proximate a top end of the stem of the venturi reaction chamber 412. As will be described in greater detail below, the design of the venturi reaction chamber 412 assists in keeping emissions trapped within the filter cartridge assembly 400 for a longer period of time, thereby increasing the effectiveness with which the emissions can be filtered.

The narrower stem portion of the venturi reaction chamber 412 is surrounded by a cylindrical mesh filter 416. The stem portion of the venturi reaction chamber 412 and the cylindrical mesh filter 416 are inserted into a diverter 418. The diverter 418 is surrounded by a ribbed enclosure 419. The ribbed enclosure 419 centers the diverter 418 within the main enclosure body 414. The openings in the ribbed enclosure 419 allow emissions to circulate around the area between the outer surface of the diverter 418 and the inner surface of the main enclosure body 414.

It can be seen in FIG. 4 that the diverter 418 has a cylindrical body, and a conical bottom portion. The diverter 418 is enclosed on the bottom and open on the top. As emissions exit the stem of the venturi reaction chamber 412, they are directed towards and reflected off of the conical bottom portion of the diverter 418 back up into the cylindrical body of the diverter 418. As emissions flow through the cylindrical body of the diverter 418, the cylindrical mesh filter 416 encourages the emissions to condense into condensate. Some of the remaining emissions are pulled back into venturi reaction chamber 412 via openings 413, while some emissions are permitted to escape out of the top of the diverter 418. Any emissions that escape out of the top of the diverter 418 eventually travel downwards around the outer surface of the diverter 418 (via openings in the ribbed enclosure 419) towards a HEPA filter 420. In some embodiments, the HEPA filter 420 is a 0.25 micron HEPA filter. In certain embodiments, a carbon filter can be layered with the HEPA filter 420 to assist in removing any remaining odors. The HEPA filter 420 (and a carbon filter if there is one) can be secured between the vented outlet cap 422 and the ribbed enclosure 419. Once they have passed through the HEPA filter 420, filtered emissions exit the filter cartridge assembly 400 via the vented outlet cap 422.

FIG. 5A illustrates a plan view of the filter cartridge assembly 400. FIG. 5B illustrates a cross-sectional view of the filter cartridge assembly 400 along the line 5B-5B of FIG. 5A, and FIG. 5C illustrates a cross-sectional view of the filter cartridge assembly 400 along the line 5C-5C of FIG. 5A. FIG. 5B illustrates the filter cartridge assembly in its fully assembled form. FIG. 5C illustrates the partition walls that are formed within the air separator inlet 408.

FIG. 6A illustrates a plan view of the filter cartridge assembly 400, and FIG. 6B illustrates a cross-sectional view of the filter cartridge assembly 400 along the line 6B-6B of FIG. 6A. FIG. 6B includes arrows to indicate how emissions work their way through the filter cartridge assembly 400, as was previously described above with reference to FIG. 4. Emissions are blown into a mouthpiece of an electronic smoking device, and pass through an outlet check valve. Once through the outlet check valve, emissions enter the filter cartridge assembly 400 via an inlet 402. The emissions then pass through a mesh screen/demister 406, and then through an air separation inlet 408. After exiting the air separation inlet 408, emissions pass through a polyester felt filter 410 into a mouth portion of a venturi reaction chamber 412. Emissions accelerate through a narrower stem portion of the venturi reaction chamber 412. As emissions accelerate through the venturi reaction chamber 412, surrounding air inside the filter cartridge assembly 400 is pulled into the venturi reaction chamber 412 via openings 413. As emissions exit the bottom stem portion of the venturi reaction chamber 412, they bounce off of a conical bottom portion of a diverter 418. Emissions bounce off the conical bottom portion of the diverter 418 into a cavity 417 defined by an outer surface of the venturi reaction chamber 412 and an inner surface of the cylindrical body of the diverter 418. Also contained within the cavity 417 is a cylindrical mesh filter 416. As emissions travel up through the cavity 417, the cylindrical mesh filter 416 causes some of the emissions to condense into condensate. Some emissions within the cavity 417 are pulled back into the venturi reaction chamber 412 via openings 413, while some emissions escape out of the top of the diverter 418. Emissions that escape out of the top of the diverter 418 are directed back down into an outer cavity 421 defined by the inner surface of an outer enclosure 414 and the outer surface of the diverter 418, towards a HEPA filter and/or charcoal filter 420. Emissions then exit the filter cartridge assembly 400 via a vented outlet cap 422.

FIG. 6C illustrates a cross-sectional view of the filter cartridge assembly 400 along the line 6C-6C of FIG. 6A. As noted previously, the HEPA filter 420 is secured between the vented outlet cap 422 and the ribbed enclosure 419 (see FIG. 4). However, in order for a HEPA filter 420 to work effectively, there must be sufficient surface area of the HEPA filter 420 exposed so that emissions can pass through the HEPA filter 420. As such, narrow strips of material (e.g., ribs) can be utilized to secure the HEPA filter 420 in place between the vented outlet cap 422 and the ribbed enclosure 419 while still ensuring sufficient open surface area for emissions to pass through and be filtered. In certain embodiments, no more than 23.5% of the HEPA filter 420's surface area should be covered, such that emissions can pass through at least 76.5% of the HEPA filter's surface area. For example, if the total surface area of the HEPA filter 420 shown in FIG. 6C is approximately 0.460 sq. in., no more than 0.108 sq. in. of the HEPA filter 420's surface should be covered/obstructed by the vented outlet cap 422 and the ribbed enclosure 419.

Figure 7A:
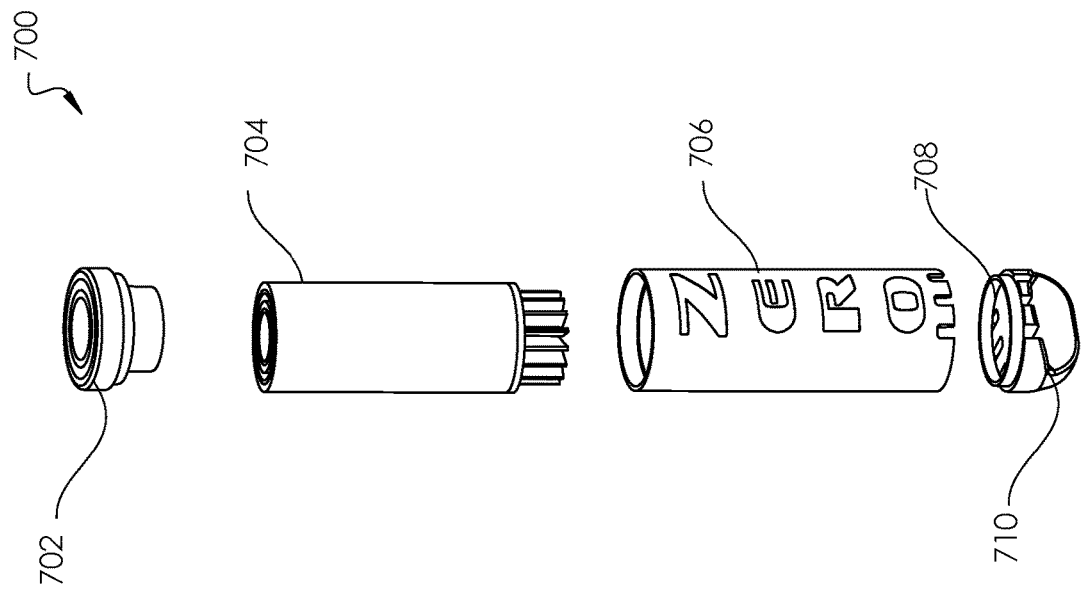
FIG. 7A illustrates an exploded view of a filter cartridge assembly, according to an embodiment of the present disclosure.

FIG. 7A illustrates an exploded view of a filter cartridge assembly 700, in accordance with an embodiment of the present disclosure. In certain embodiments, the filter cartridge assembly 700 can be used as the filter cartridge assembly 114 of FIG. 1B. Filter cartridge assembly 400, discussed above, utilized a combination of condensator design and filters to both condense emissions into condensate and filter out particulates and odors. Filter cartridge assembly 700, which is depicted in FIGS. 7-9, utilizes more of a capillary filtration approach. As can be seen in FIG. 7A, the filter cartridge assembly 700 has, similar to the filter cartridge assembly 400, a main enclosure body 706 sealed at the top by an inlet cap 702 and at the bottom by a vented outlet cap 710. Housed within the main enclosure body 706 is a concentric 4-stage filter 704.

Figure 7B:
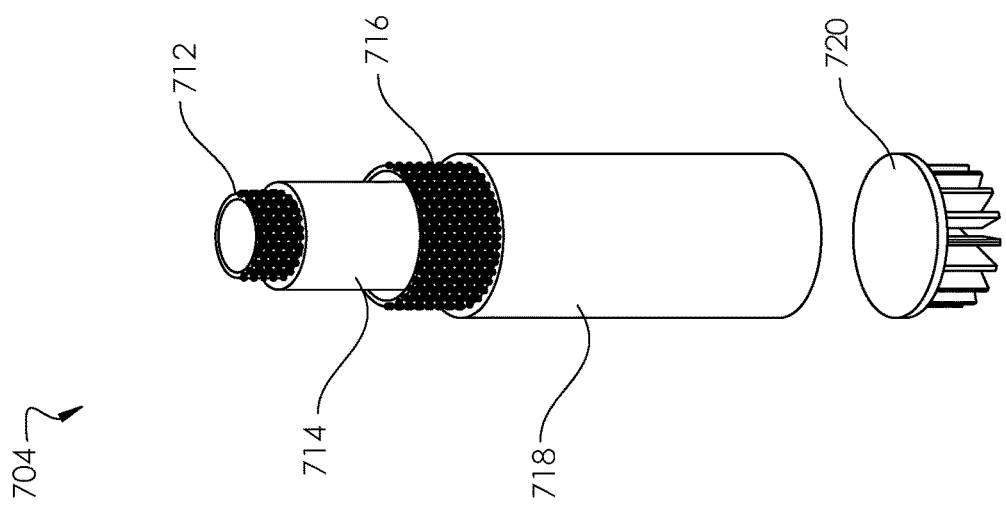
FIG. 7B illustrates an exploded view of a concentric 4 stage filter, according to an embodiment of the present disclosure.

FIG. 7B illustrates an exploded view of the concentric 4-stage filter 704. The concentric 4-stage filter 704 includes an inner mesh substrate 712, surrounded by a large-diameter foam 714 (in this example, a 1 micron foam), which is surrounded by an outer mesh substrate 716, which is surrounded by a small-diameter foam 718 (in this example, a 0.25 micron foam). These four, concentric layers are secured to a base 720. As will be described in greater detail with reference to FIGS. 8 and 9, when emissions enter the concentric 4 stage filter 704, they are pushed outwards, away from a central axis of the concentric 4 stage filter 704. As emissions are pushed outwards, they must pass through the four layers of the concentric 4-stage filter 704. Each layer filters and/or condenses the emissions to remove particulate matter and odors. While the example embodiment presented has four concentric layers, it should be understood that fewer or more concentric layers can be used.

As seen in FIG. 7A, a HEPA filter 708 is secured between the base 720 and the vented outlet cap 710. Once emissions have passed through the concentric 4 stage filter, they pass through the HEPA filter 708 and clean, filtered emissions exit the vented outlet cap 710. As discussed above, narrow ribs on the base 720 and the vented outlet cap 710 can secure the HEPA filter 708 in place while still allowing for sufficient open surface area that emissions can pass through the HEPA filter 708.

Figure 8B:
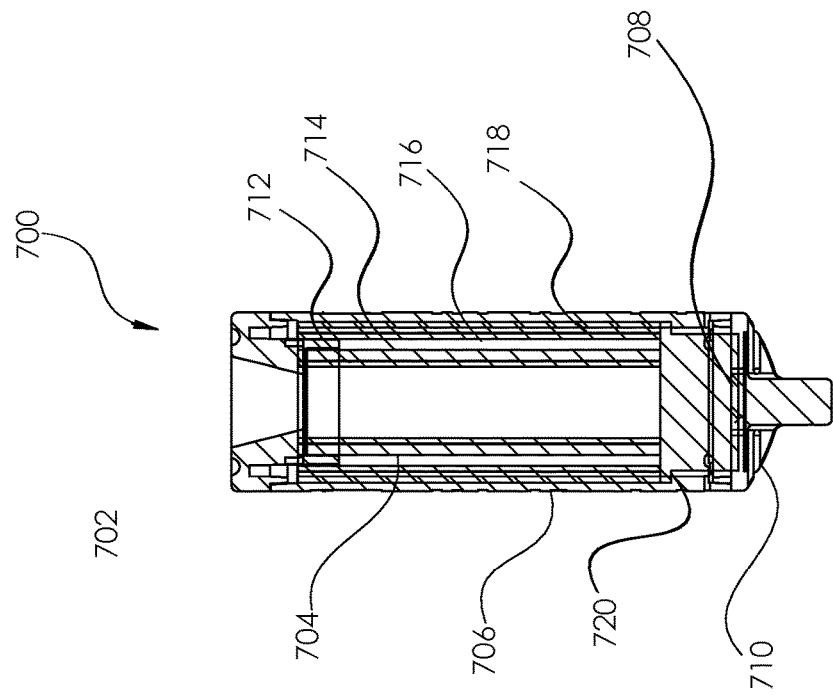
FIG. 8B illustrates a cross-sectional view of the filter cartridge assembly of FIG. 8A taken along line 8B-8B of FIG. 8A, according to an embodiment of the present disclosure.
Figure 8A:
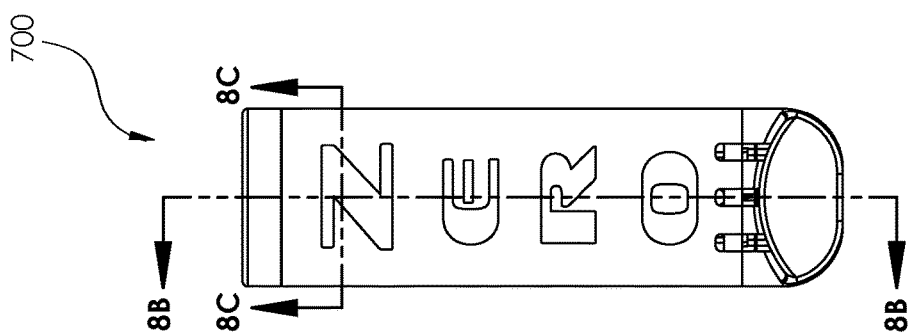
FIG. 8A illustrates a plan view of the filter cartridge assembly of FIG. 7A, according to an embodiment of the present disclosure.
Figure 8C:
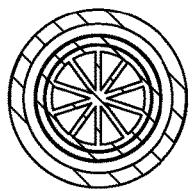
FIG. 8C illustrates a cross-sectional view of the filter cartridge assembly of FIG. 8A taken along line 8C-8C of FIG. 8A, according to an embodiment of the present disclosure.

FIG. 8A illustrates a plan view of the filter cartridge assembly 700. FIG. 8B illustrates a cross-sectional view of the filter cartridge assembly 700 taken along line 8B-8B of FIG. 8A. FIG. 8C illustrates a cross-sectional view of the filter cartridge assembly 700 taken along line 8C-8C of FIG. 8A. As can be seen in the figures, there are four layers of porous, filtering materials (alternating layers of mesh screens and foams) through which emissions can pass to be filtered.

Figure 9B:
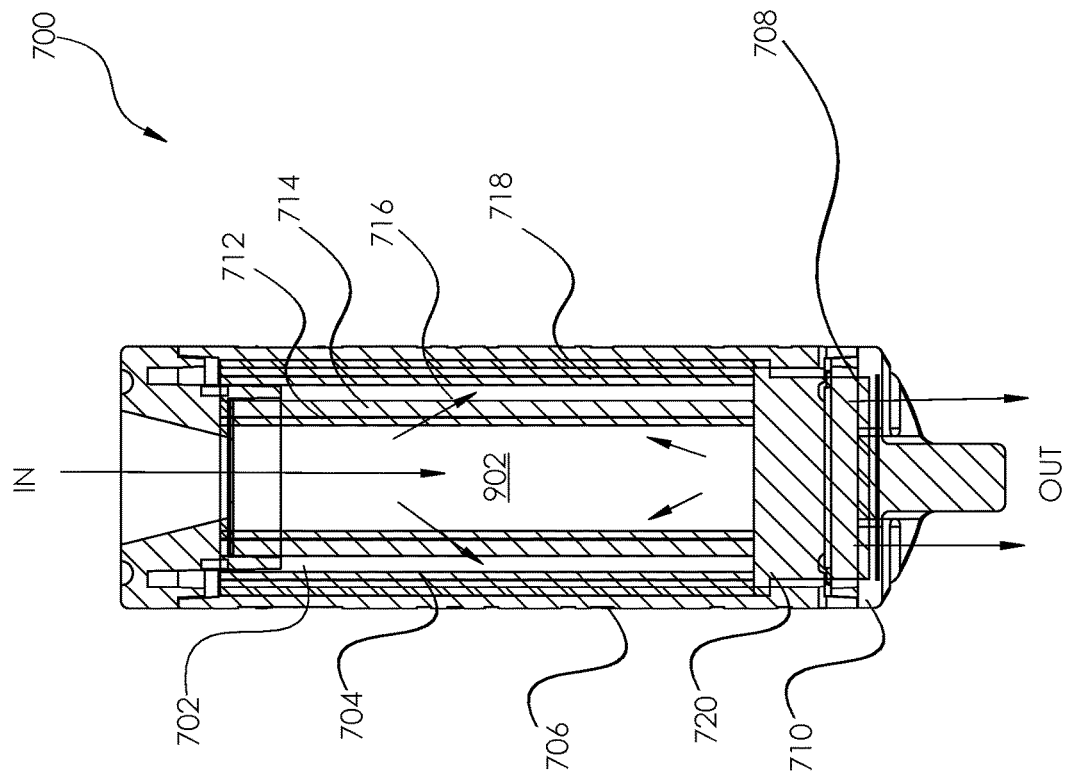
FIG. 9B illustrates a cross-sectional view of the filter cartridge assembly of FIG. 9A taken along line 9B-9B of FIG. 9A, according to an embodiment of the present disclosure.
Figure 9A:
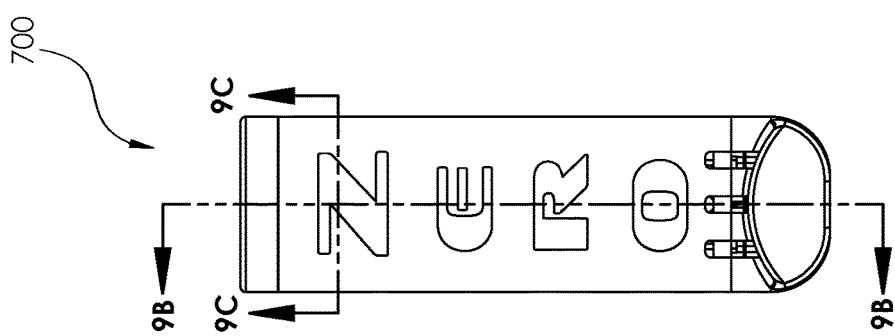
FIG. 9A illustrates a plan view of the filter cartridge assembly of FIG. 7A, according to an embodiment of the present disclosure.
Figure 9C:
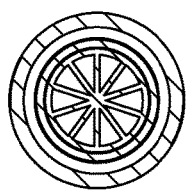
FIG. 9C illustrates a cross-sectional view of the filter cartridge assembly of FIG. 9A taken along line 9C-9C of FIG. 9A, according to an embodiment of the present disclosure.

FIG. 9A illustrates a plan view of the filter cartridge assembly 700. FIG. 9B illustrates a cross-sectional view of the filter cartridge assembly 700 taken along line 9B-9B of FIG. 9A. FIG. 9C illustrates a cross-sectional view of the filter cartridge assembly 700 taken along line 9C-9C of FIG. 9A.

FIG. 9B illustrates a general airflow path taken by emissions as they pass through the filter cartridge assembly 700. Emissions enter through the top of the filter cartridge assembly 700, and enter an inner cavity 902. In certain embodiments, as seen in FIGS. 8C and 9C, the inner cavity 902 may be divided into one or more segments by one or more partitions. The lower end of the inner cavity 902 is sealed by the base 720, and the top of the filter cartridge assembly 700 is sealed by an exhale check valve (such as the outlet check valve 214 of FIGS. 2-3). As such, emissions are forced through the porous filtering layers of the concentric 4 stage filter 704 which define the lateral walls of the inner cavity 902. As a user exhales into the filter cartridge assembly 700, emissions are forced through the inner mesh substrate 712, the large diameter foam 714, the outer mesh substrate 716, and the small diameter foam 718. The mesh substrates 712, 716 force some of the emissions to condense into condensate, and provide some filtering ability, while the foam layers 714, 718 filter out particulate matter and odors. Once through all four layers, emissions can pass through the base 720 and the HEPA filter 708, and then out of the vented outlet cap 710.

Figure 10:
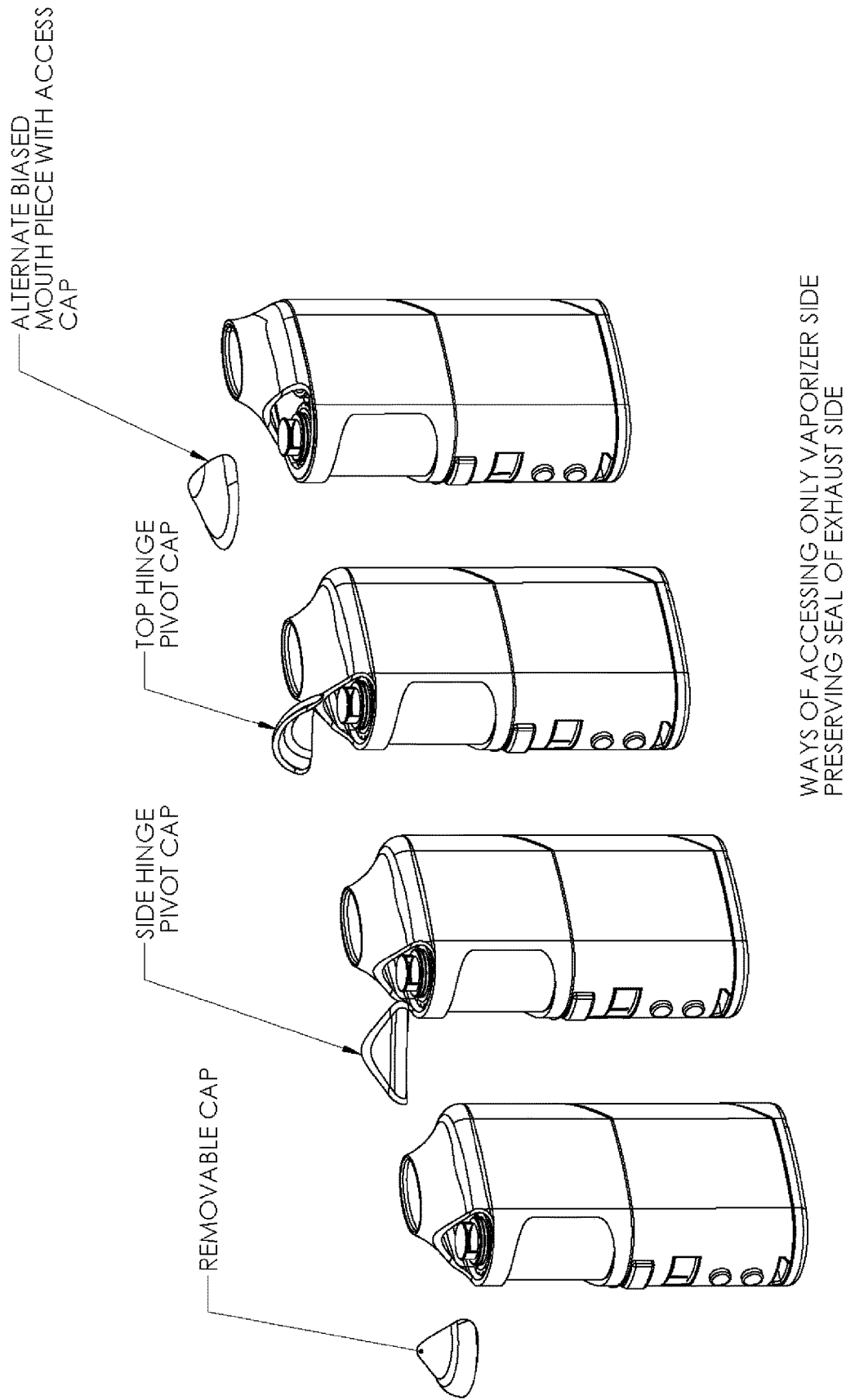
FIG. 10 illustrates perspective views of various electronic smoking devices having various ways of accessing a vaporizer portion of each electronic smoking device, according to various embodiments of the present disclosure.

FIG. 10 illustrates perspective views of various electronic smoking devices, each of which includes a different way of accessing a vaporizer portion of an electronic smoking device, according to various embodiments of the present disclosure. As discussed above, it is generally desirable that once emissions are exhaled into the electronic smoking device 100, they are sealed inside and do not leak out without having gone through the filtering mechanisms of the filter cartridge assembly. As such, in certain embodiments, a diverter valve, such as the diverter valve 210 of FIG. 2, may be sealed to a mouthpiece, such as the mouthpiece 102 of FIG. 2, so as to prevent leakage up through the diverter valve and out of the mouthpiece. However, users will generally need to access the vaporizer portion of an electronic smoking device. For example, in the example embodiment shown in FIGS. 2-3, users may have to change and/or refill the material in the cooker chamber 107. In order to ensure that the seal between the diverter valve 210 and the mouthpiece 102 remains secure and leak-proof, users may be given access to the vaporizer portion of an electronic smoking device without disturbing the seal between the diverter valve 210 and the mouthpiece 102. In FIG. 10, four different embodiments are shown by which a user can access a vaporizer portion without removing the mouthpiece 102. In the leftmost embodiment, a removable cap is provided which provides access to the vaporizer portion without removing the mouthpiece 102. Similarly, in the two center embodiments, a side-hinge cap and a top-hinge cap provide access to the vaporizer portion. In the rightmost embodiment, the mouthpiece 102 has been offset. The mouthpiece 102 is no longer centered, and is set towards the filter cartridge assembly portion of the electronic smoking device so as to provide more convenient access to the vaporizer portion.

It should be noted that, while the various example embodiments presented in the figures and discussed above have utilized an open tank electronic smoking device in which a user can access and refill materials in the cooker chamber, such example embodiments are provided for ease of explanation, and the present disclosure is not limited to such embodiments. The various features and improvements discussed herein such as, for example, the onboard filtering solutions and bi-directional diverter valving systems, can be implemented on any electronic smoking device, non-electronic smoking device, and/or vaping device of any form factor, shape, and/or size. For example, the technologies disclosed herein can be applied to open tank eliquid devices, closed tank eliquid devices, as well as devices designed for use with any material, including liquid, wax, and dry leaf materials such as cannabis.

Figure 11:
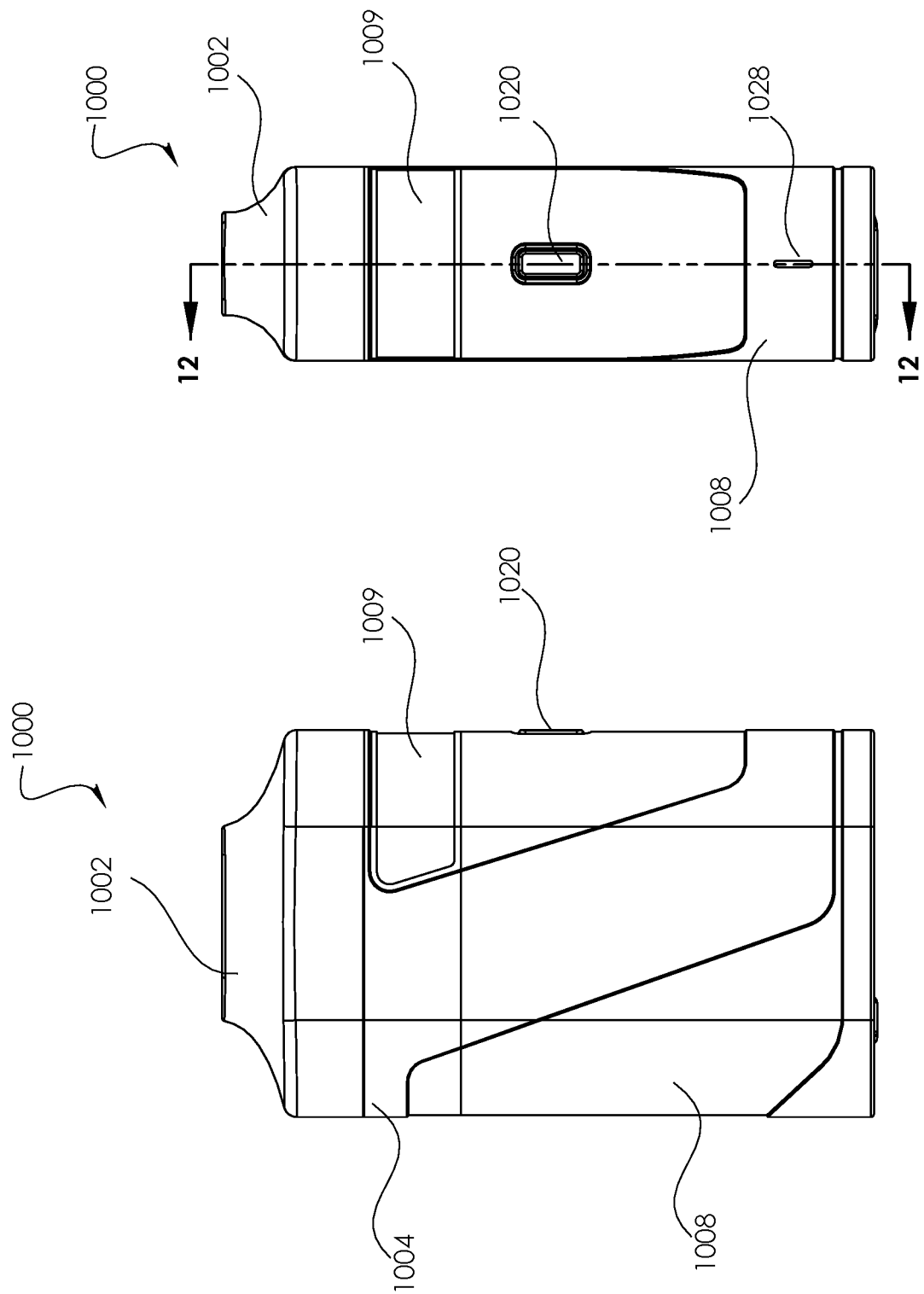
FIG. 11A illustrates a side plan view of an electronic smoking device, according to an embodiment of the present disclosure.
FIG. 11B illustrates a front plan view of the electronic smoking device of FIG. 11A, according to an embodiment of the present disclosure.

FIG. 11A and FIG. 11B illustrate, respectively, a side plan view and a front plan view of another electronic smoking device 1000, according to an embodiment of the present disclosure. The electronic smoking device 1000 includes a mouthpiece 1002 secured to a mid-enclosure 1004. In certain embodiments, the mouthpiece 1002 can be a disposable and/or replaceable component. In various embodiments, different mouthpieces 1002 can be flavored with different flavors such that users can select and install a mouthpiece 1002 based on a flavor of the user's choosing, and can replace the mouthpiece with a new one should the user wish to experience a different flavor. It should be understood that this feature can be applied to any of the various mouthpieces disclosed herein, and, similarly, any features described with respect to any particular component or embodiments described herein can be applied to any other similar components or embodiments described herein.

The mid-enclosure 1004 houses a cooker chamber that is configured to contain a material to be heated and vaporized, such as liquid, oil, flower, or leaf material. The mid-enclosure 1004 can include a transparent portion 1009 so that a user can view material contained within the cooker chamber. The electronic smoking device 1000 includes an igniter button 1020 that a user can press to heat and vaporize material in the cooker chamber, and a charging port 1028 to charge the electronic smoking device 1000.

Figure 12:
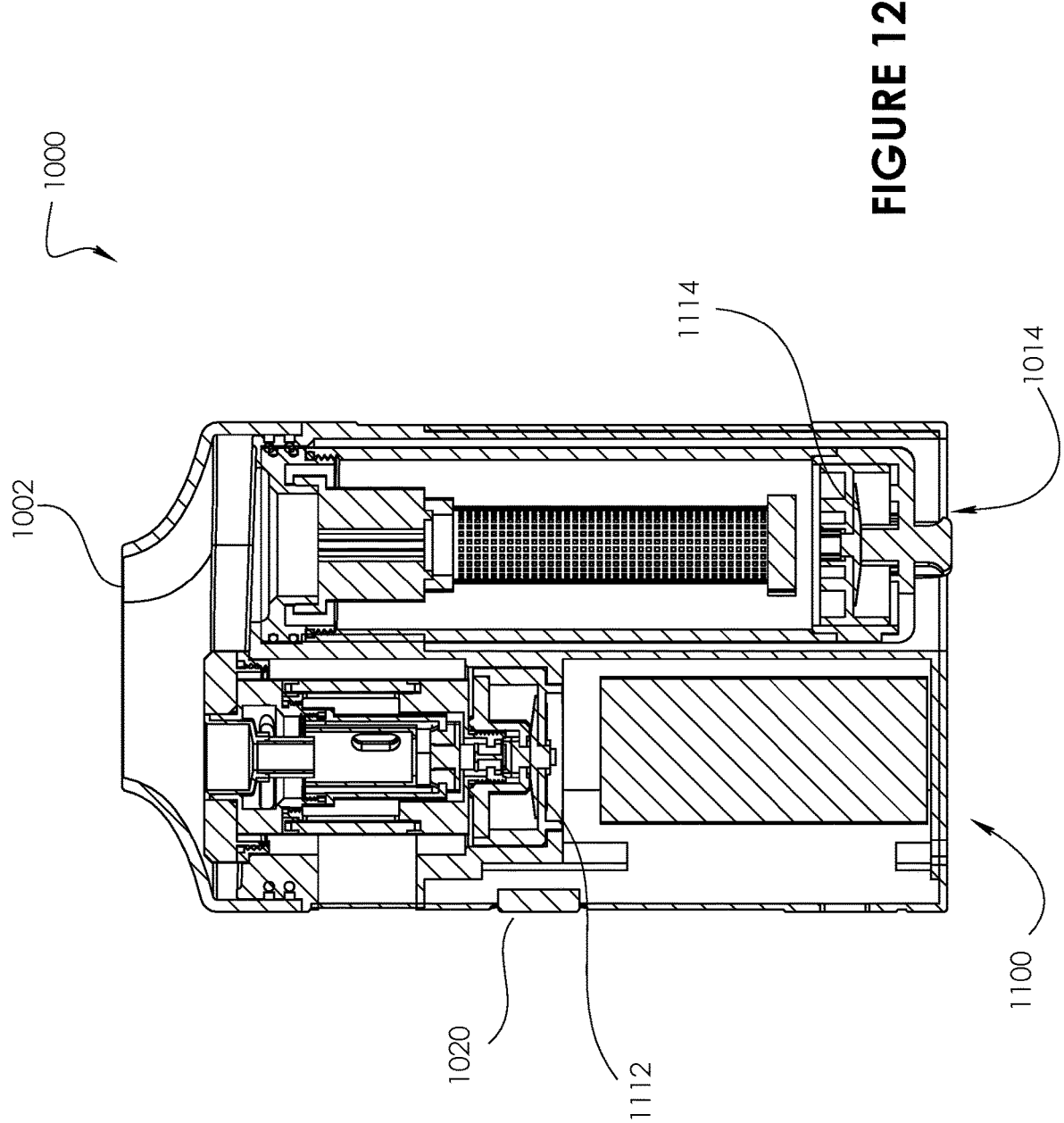
FIG. 12 illustrates a cross-sectional view of the electronic smoking device of FIG. 11B taken along line 12-12 of FIG. 11B, according to an embodiment of the present disclosure.

FIG. 12 illustrates a cross-sectional view of the electronic smoking device 1000 taken along a line 12-12 of FIG. 11B, according to an embodiment of the present disclosure. In FIG. 12, it can be seen that a filter portion comprising a filter cartridge assembly 1014 occupies one side of the electronic smoking device 1000, and a vaporizer portion 1100 occupies the other side of the electronic smoking device 1000. In various embodiments, the filter cartridge assembly 1014 can be a disposable and/or replaceable component such that users can periodically replace the filter cartridge assembly 1014 with a new, fresh filter cartridge assembly.

It can be seen that, in general, the structure of the electronic smoking device 1000 is fairly similar to the electronic smoking device 100 described earlier in this disclosure. However, one notable difference in this embodiment is the placement of an inlet check valve 1112 within the vaporizer portion 1100 and an outlet check valve 1114 within the filter cartridge assembly 1014. In a previous embodiment depicted in FIG. 2B and FIGS. 3A-C, an inlet check valve 212 and an outlet check valve 214 were positioned within a mouthpiece 102. However, in this embodiment, these components have been moved into the vaporizer portion 1100 and the filter cartridge assembly 1014, respectively. The various components of the vaporizer portion 1100 and the filter cartridge assembly 1014 will now be described in greater detail with reference to FIGS. 13, 14, and 15A-D.

Figure 13:
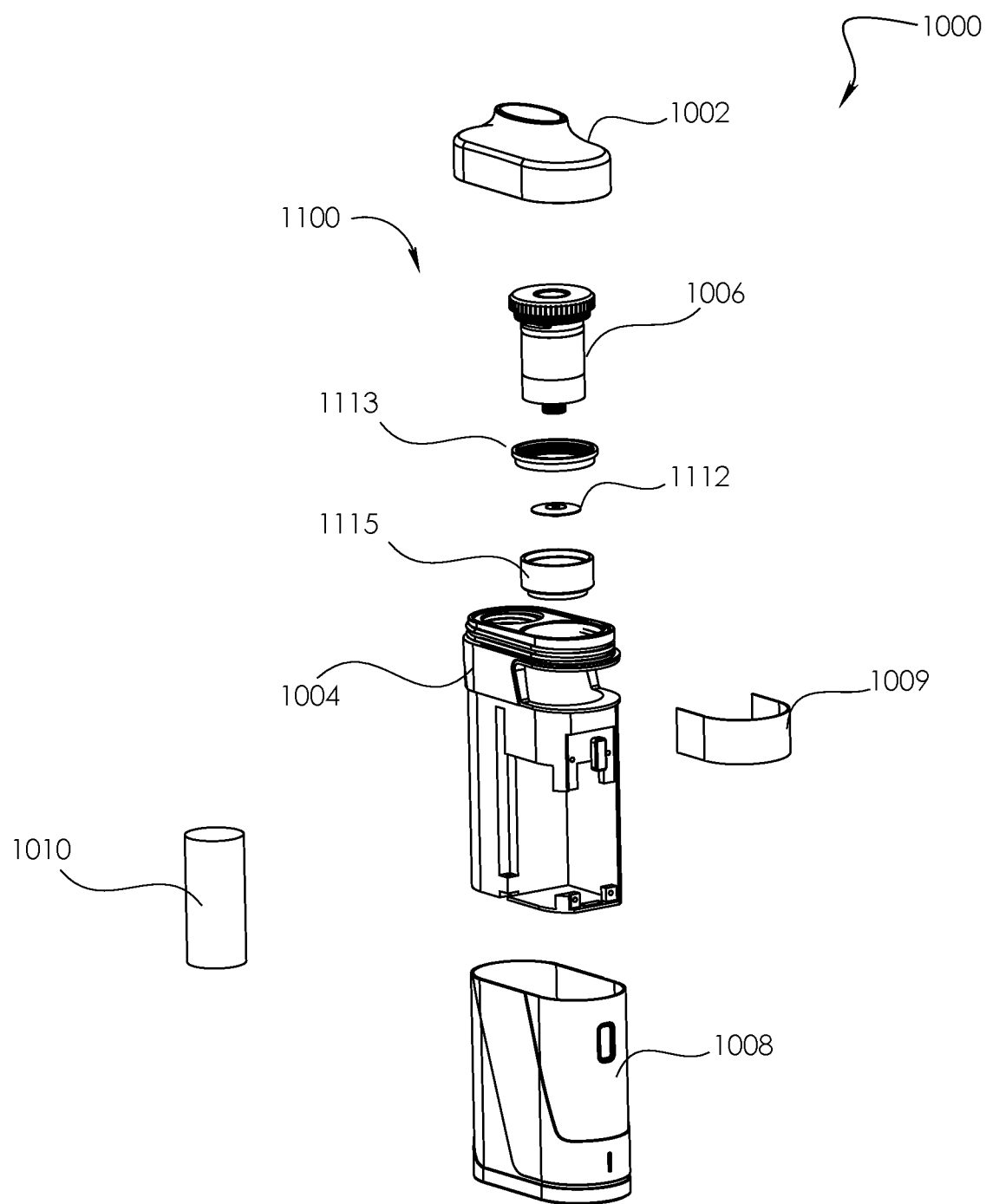
FIG. 13 illustrates an exploded view of the electronic smoking device of FIG. 11A, according to an embodiment of the present disclosure.

FIG. 13 illustrates an exploded view of the electronic smoking device 1000, without the filter cartridge assembly 1014, and with particular emphasis on the vaporizer portion 1100, according to an embodiment of the present disclosure. FIG. 13 depicts the mouthpiece 1002, which is secured to the mid-enclosure 1004. The mid-enclosure 1004 is at least partially enclosed by an external housing 1008. The mid-enclosure 1004 houses a cooker chamber 1006, which is configured to contain a material to be heated and vaporized. The cooker chamber 1006 also includes a heating element, such as a coil, to heat and vaporize material contained therein. The heating element may draw power from a battery 1010. The cooker chamber 1006 is sealed by a seal 1113. The seal 1113 and a valve housing 1115 are secured together to house an inlet check valve 1112. The inlet check valve 1112 is a one way valve that allows vapors to escape the cooker chamber 1006 into the mouthpiece 1002 when a user inhales on the mouthpiece 1002, but substantially blocks and/or prohibits emissions from entering the cooker chamber 1006 or the vaporizer portion 1100 when the user exhales into the mouthpiece 1002. For example, when a user inhales, the inlet check valve 1112 can lift away from the valve housing 1115, allowing air to flow into the cooker chamber 1006 and out of the mouthpiece 1002. When the user exhales, the inlet check valve 1112 can be pushed against the valve housing 1115, preventing any air from entering the cooker chamber 1006 or the vaporizer portion 1100.

Figure 14:
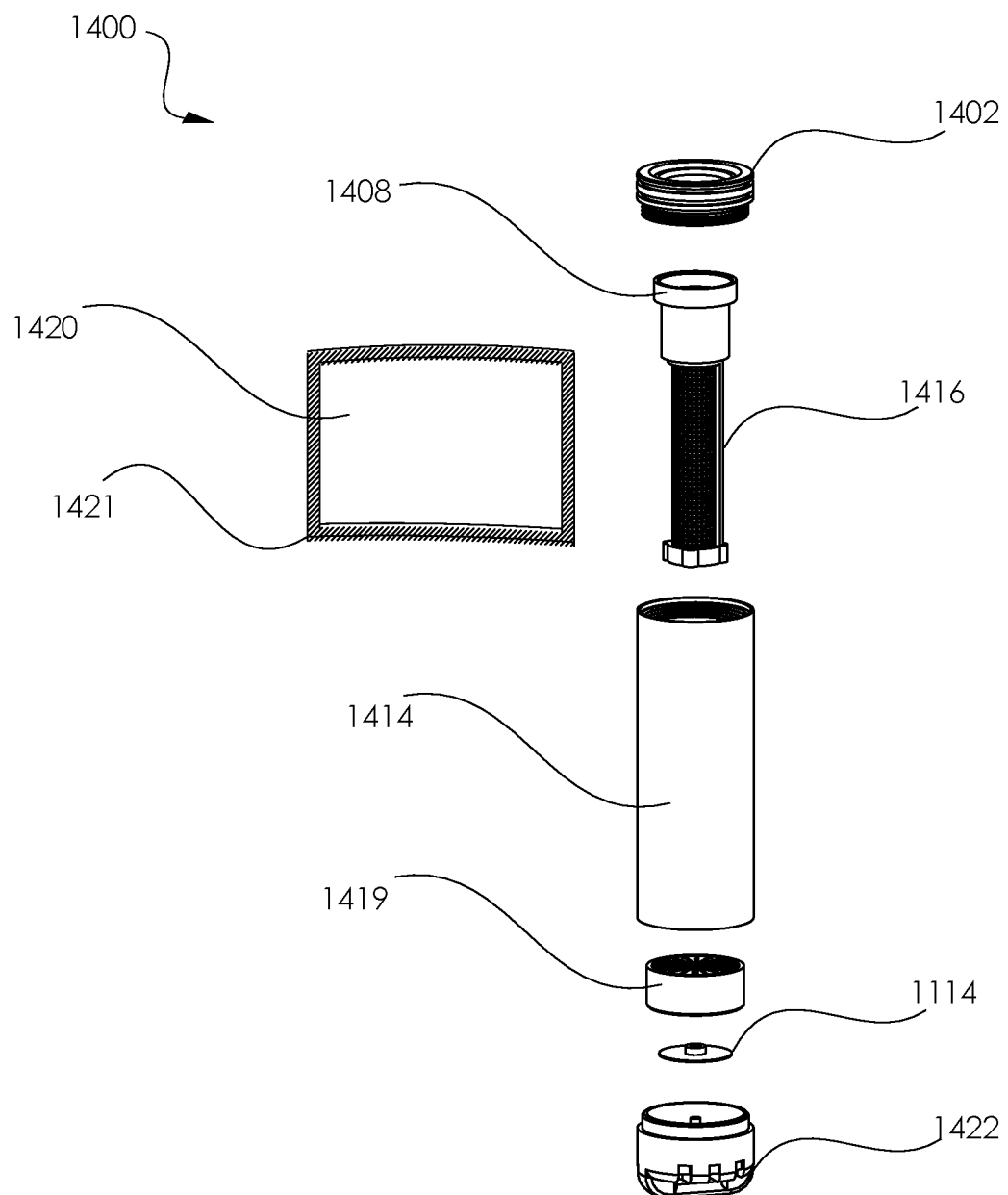
FIG. 14 illustrates an exploded view of a filter cartridge assembly, according to an embodiment of the present disclosure

FIG. 14 illustrates an exploded view of a filter cartridge assembly 1400, according to an embodiment of the present disclosure. In various embodiments, the filter cartridge assembly 1400 may be used as the filter cartridge assembly 1014 of FIG. 12. In various embodiments, the filter cartridge assembly 1400 may be used in conjunction with any of the various electronic smoking device embodiments described herein.

The filter cartridge assembly 1400 includes an open-ended cylindrical outer body 1414, which is at least partially enclosed at the top by an inlet cap 1402 and at least partially enclosed at the bottom by a vented outlet cap 1422. The inlet cap 1402 can, in various embodiments, be sealed with O-rings, a quarter turn lock, and/or a threaded seal with the outer body 1414, or any other appropriate sealing mechanisms, to form a leak-free seal. Between the inlet cap 1402 and the vented outlet cap 1422, and housed within the main enclosure body 1414, are various filtering mechanisms that assist in removing odors and particulate matter from emissions blown into the filter cartridge assembly 1400. Emissions are received into the filter cartridge assembly 1400 via the inlet cap 1402. Once the emissions pass through various filtering mechanisms housed within the main enclosure body 1414, clean, filtered emissions are emitted via the vented outlet cap 1422.

In the example embodiment shown in FIG. 14, emissions pass through the inlet cap 1402 into an air separator 1408. The air separator 1408 can be an elongated tube that is divided into sections by partition walls, similar to the air separator inlet 408 described above with reference to FIG. 4. The air separator 1408 divides exhaled emissions into various sections, and provides surface area that encourages condensation of the emissions. Once emissions pass through the air separator 1408, they pass through cylindrical mesh filter 1416. In various embodiments, the mesh filter 1416 may comprise a stainless steel material, plastic, and/or polymer material. The mesh filter 416 is also surrounded by a HEPA filter 1420. The HEPA 1420 filter is secured and sealed to the mesh filter 1416 and/or the air separator 1408 by an adhesive 1421 that surrounds the perimeter of the HEPA filter 1420. Once emissions pass through the HEPA filter 1420, they are pushed down towards another air separator 1419, through an outlet check valve 1114, and out through the vent cap 1422.

The air separator 1419 and the vent cap 1422 are ribbed to allow air to pass through (see, e.g. FIG. 15D), and the outlet check valve 1114 is secured between the air separator 1419 and the vent cap 1422. The outlet check valve 1114 is a one way valve that acts opposite the inlet check valve 1112 described above. The outlet check valve 1114 allows a user to exhale air into the mouthpiece 1002 and out through the filter cartridge assembly 1400, but substantially blocks and/or prohibits air from passing through the filter cartridge assembly 1400 into the mouthpiece 1002 when a user inhales on the mouthpiece 1002. For example, when a user exhales, the outlet check valve 1114 can lift away from the air separator 1419, allowing air to flow into and through the filter cartridge assembly 1400 and out of the vented outlet cap 1422. When the user inhales, the outlet check valve 1114 can be pushed against the air separator 1419, preventing any air from moving through the filter cartridge assembly 1400.

Figure 15B:
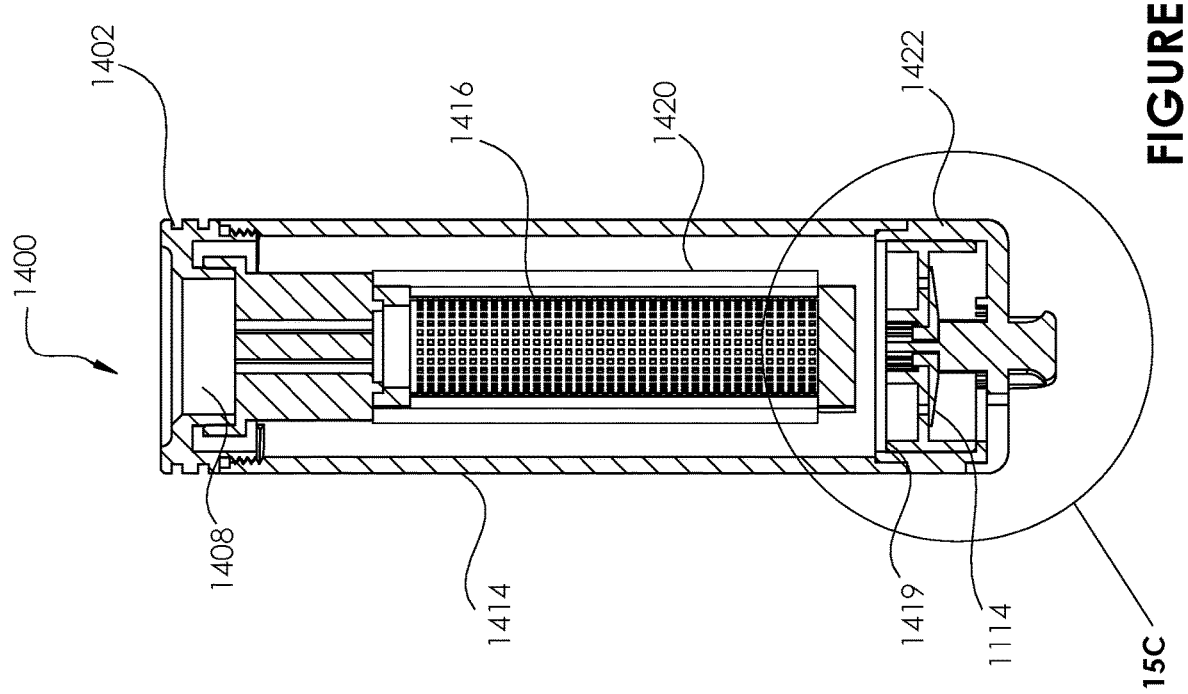
FIG. 15B illustrates a cross-sectional view of the filter cartridge assembly of FIG. 15A taken along line 15B-15B of FIG. 15A, according to an embodiment of the present disclosure.
Figure 15A:
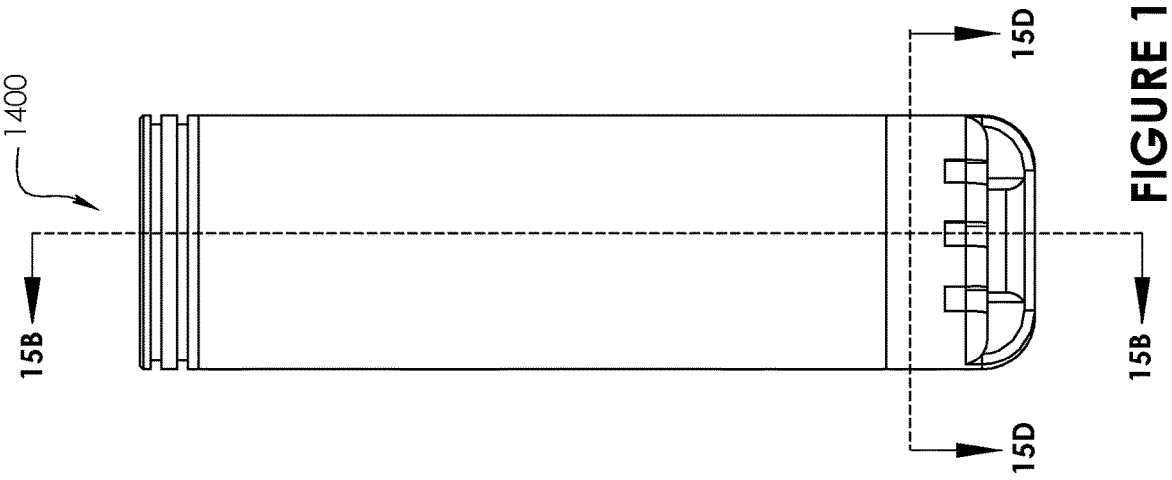
FIG. 15A illustrates a plan view of the filter cartridge assembly of FIG. 14, according to an embodiment of the present disclosure.

FIG. 15A illustrates a plan view of the filter cartridge assembly 1400, according to an embodiment of the present disclosure. FIG. 15B illustrates a cross-sectional view of the filter cartridge assembly 1400 along the line 15B-15B of FIG. 15A. FIG. 15C illustrates a close-up view of the filter cartridge assembly 1400. It can be more clearly seen in FIGS. 15B and 15C that when a user exhales into a mouthpiece of an electronic smoking device (such as the mouthpiece 1002 of the electronic smoking device 1000 of FIG. 12), emissions from the user enter the filter cartridge assembly 1400 through the inlet cap 1402 into the air separator 1408. Emissions are then pushed through the mesh filter 1416 and the HEPA filter 1420. The filtered emissions then pass through the air separator 1419 and the outlet check valve 1114, and out of the filter cartridge assembly 1400 via the vent cap 1422.

Figure 15D:
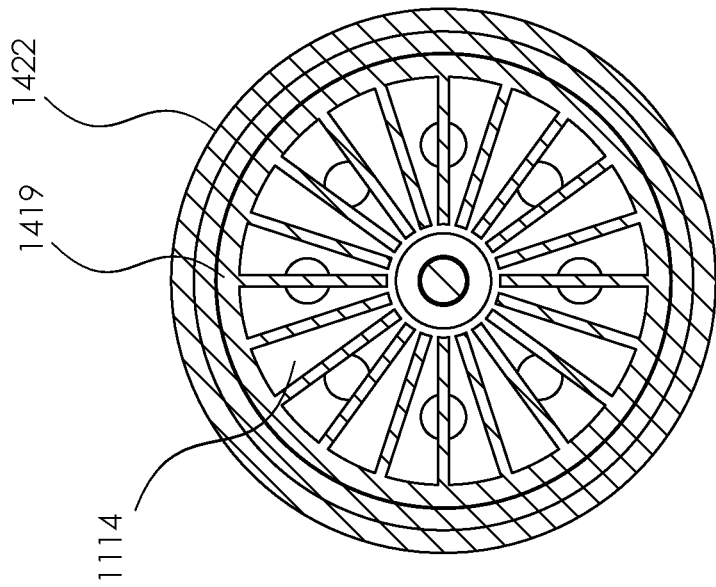
FIG. 15D illustrates a cross-sectional view of the filter cartridge assembly of FIG. 15C taken along line 15D-15D of FIG. 15A, according to an embodiment of the present disclosure.
Figure 15C:
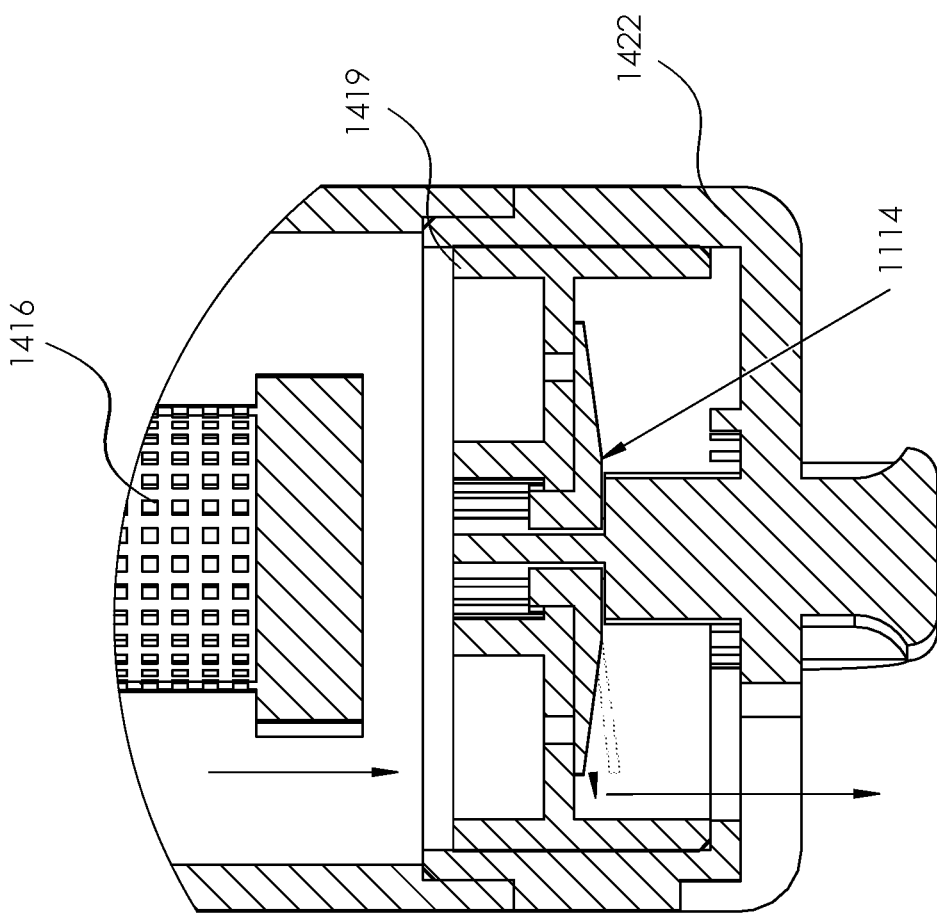
FIG. 15C illustrates a close-up view of the filter cartridge assembly of FIG. 15B, according to an embodiment of the present disclosure.

FIG. 15D illustrates a cross-sectional view of the filter cartridge assembly 1400 along the line 15D-15D of FIG. 15A. FIG. 15D shows openings in the air separator 1419 and the vented outlet cap 1422 that allow the two components to secure the outlet check valve 1114 while still allowing air to pass through. When a user inhales on an electronic smoking device, the outlet check valve 1114 seals against the air separator 1419 to prevent air from flowing through the filter cartridge assembly 1400. When a user exhales on an electronic smoking device, the outlet check valve 1114 lifts away from the air separator 1419, allowing air to flow through the filter cartridge assembly 1400.

FIG. 16A illustrates a perspective view of an electronic smoking device 1600, according to an embodiment of the present disclosure. FIG. 16B illustrates an exploded view of the electronic smoking device 1600. The electronic smoking device 1600 includes a mouthpiece 1602 secured to a body enclosure 1604. In certain embodiments, as discussed above, the mouthpiece 1602 can be a disposable and/or replaceable component. The body enclosure houses a vaporizer cartridge assembly 1620 and a filter cartridge assembly 1630. The vaporizer cartridge assembly 1620 houses a material to be heated and vaporized. In various embodiments, the vaporizer cartridge assembly 1620 can be a removable and disposable component such that when the vaporizer cartridge assembly 1620 is substantially empty (e.g., a user has vaporized all material contained within the vaporizer cartridge assembly 1620), it can be replaced with a new vaporizer cartridge assembly. In various embodiments, the vaporizer cartridge assembly 1620 can also be a sealed assembly such that users are discouraged and/or prevented from refilling the vaporizer cartridge assembly 1620.

The body enclosure 1604 includes a display 1606. The display 1606 can be, for example, an electronic display. In another example, the display 1606 can be a transparent window through which a user can view material contained in the cartridge assembly 1620. The electronic smoking device 1600 includes an igniter button 1608 that a user can press to heat and vaporize material in the vaporizer cartridge assembly 1620, one or more LED display lights 1610, and a charging port 1612 to charge the electronic smoking device 1600. The one or more LED display lights 1610 may provide an indication of, for example, remaining battery charge left in the electronic smoking device 1600, a wattage level of the electronic smoking device 1600, and/or a remaining cartridge life for the vaporizer cartridge assembly 1620. The body enclosure 1604 also includes a removable storage cover 1614. As will be described in greater detail below, the removable storage cover 1614 can be removed to reveal a storage compartment in which, for example, additional vaporizer cartridge assemblies can be stored.

Figure 17B:
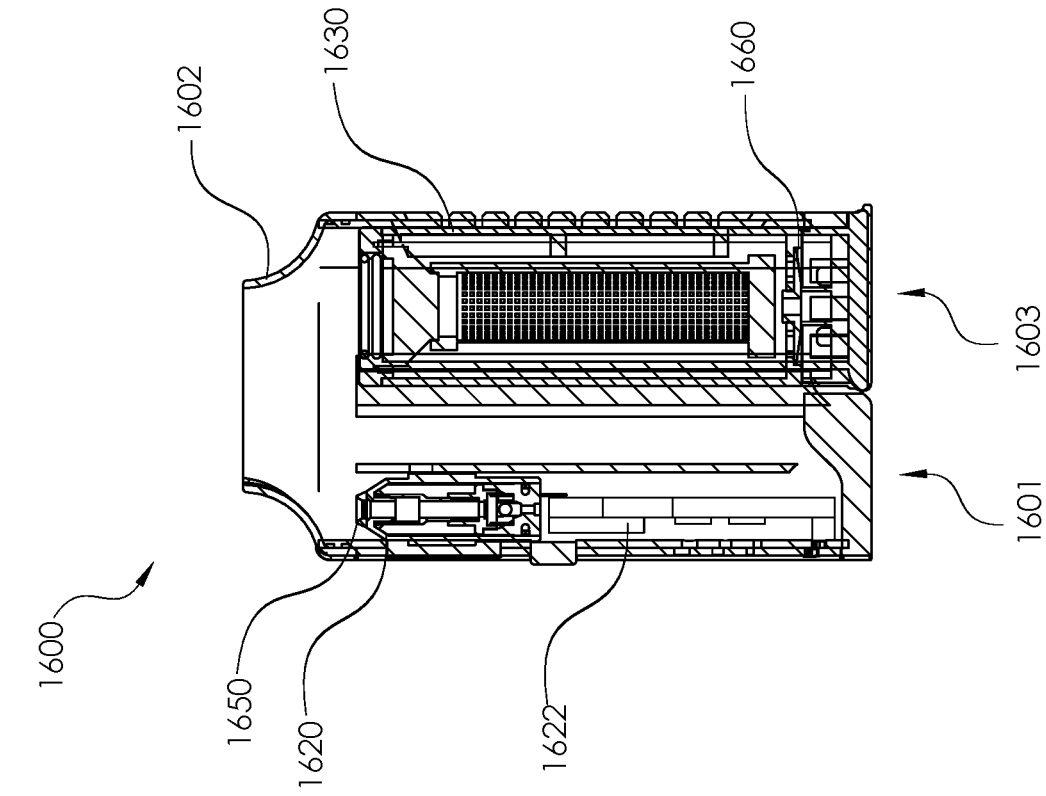
FIG. 17B illustrates a cross-sectional view of the electronic smoking device of FIG. 17A taken along line 17B-17B of FIG. 17A, according to an embodiment of the present disclosure.
Figure 17A:
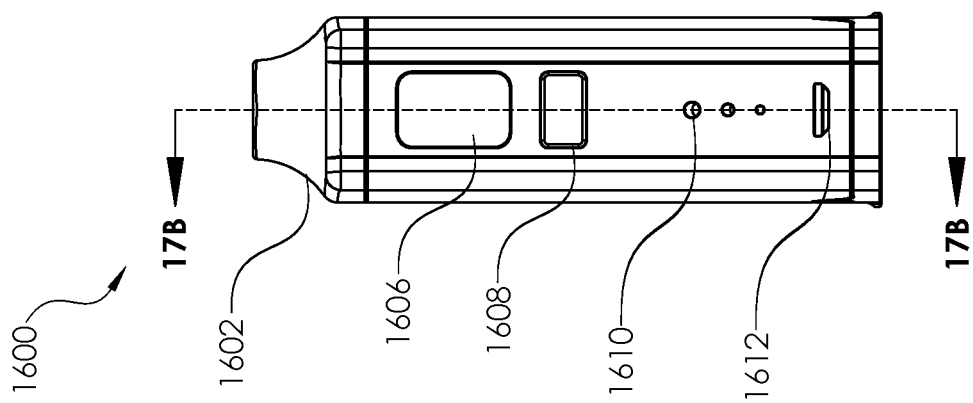
FIG. 17A illustrates a front plan view of the electronic smoking device of FIG. 16A, according to an embodiment of the present disclosure.

FIG. 17A illustrates a front plan view of the electronic smoking device 1600. FIG. 17B illustrates a cross-sectional view of the electronic smoking device 1600 taken along a line 17B-17B of FIG. 17A, according to an embodiment of the present disclosure. In FIG. 17B, it can be seen that the vaporizer cartridge assembly 1620 is connected to a PCB/battery 1622. The electronic smoking device 1600 comprises a vaporizer portion 1602, which comprises the vaporizer cartridge assembly 1620 and the PCB/battery 1622. The electronic smoking device 1600 also comprises a filter portion 1603 which comprises the filter cartridge assembly 1630. In various embodiments, both the vaporizer cartridge assembly 1620 and the filter cartridge assembly 1630 can be a disposable and/or replaceable components such that users can periodically replace the vaporizer cartridge assembly 1620 with a new vaporizer cartridge assembly, and can periodically replace the filter cartridge assembly 1630 with a new filter cartridge assembly.

Similar to the embodiments shown in FIGS. 12-15, the vaporizer cartridge assembly 1620 includes an inlet check valve 1650 and the filter cartridge assembly 1650 includes an outlet check valve 1660. Similar to other inlet check valves described herein, the inlet check valve 1620 is a one way valve that allows vapors to escape the vaporizer cartridge assembly 1620 into the mouthpiece 1602 when a user inhales on the mouthpiece 1602, but substantially blocks and/or prohibits emissions from entering the vaporizer cartridge assembly 1620 when the user exhales into the mouthpiece 1602. The outlet check valve 1660 allows a user to exhale air into the mouthpiece 1602 and out through the filter cartridge assembly 1630, but substantially blocks and/or prohibits air from passing through the filter cartridge assembly 1630 into the mouthpiece 1602 when a user inhales on the mouthpiece 1602.

Figure 18A:
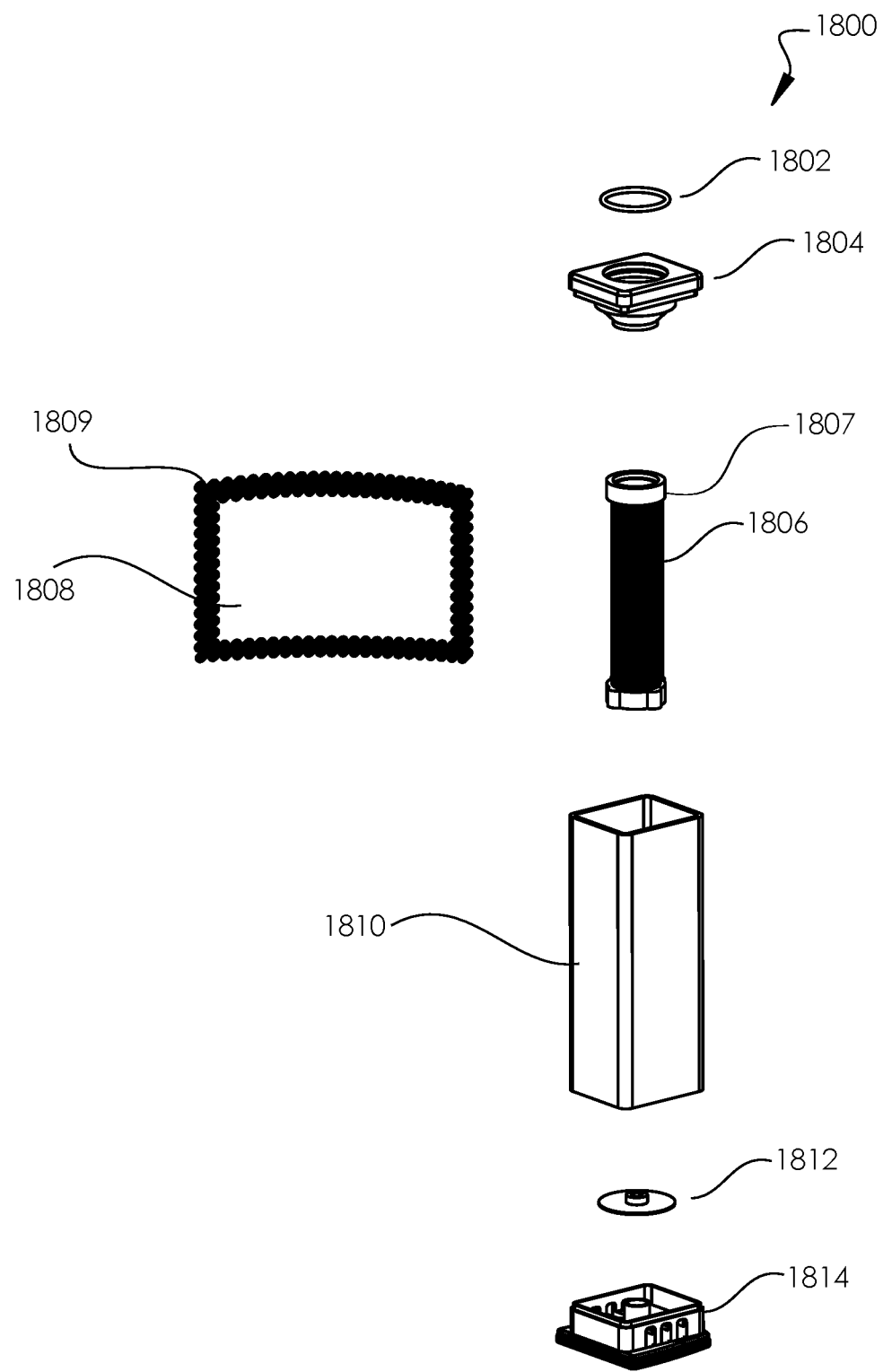
FIG. 18A illustrates an exploded view of a filter cartridge assembly, according to an embodiment of the present disclosure.
Figure 18C:
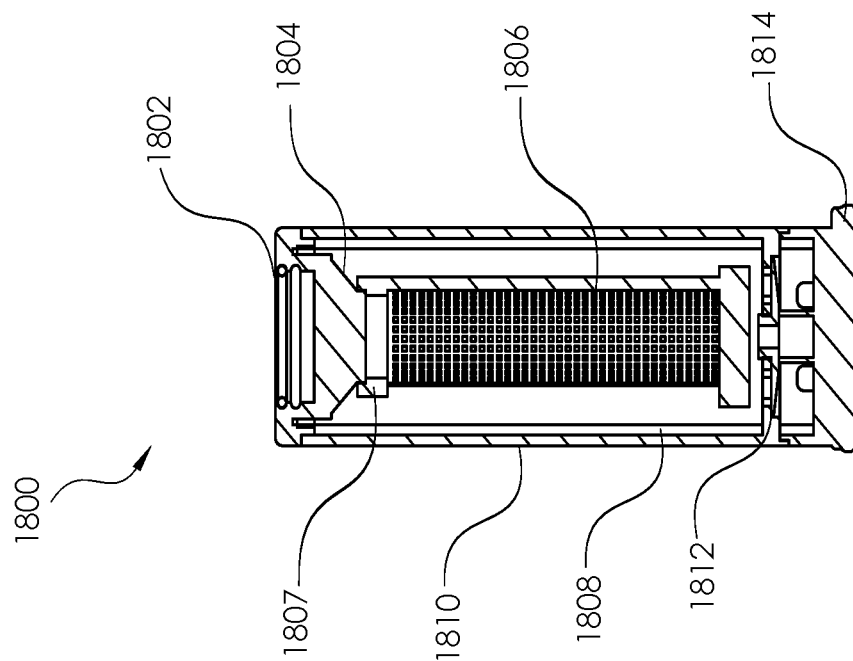
FIG. 18C illustrates a cross-sectional view of the filter cartridge assembly of FIG. 18B taken along the line 18C-18C of FIG. 18B, according to an embodiment of the present disclosure.
Figure 18B:
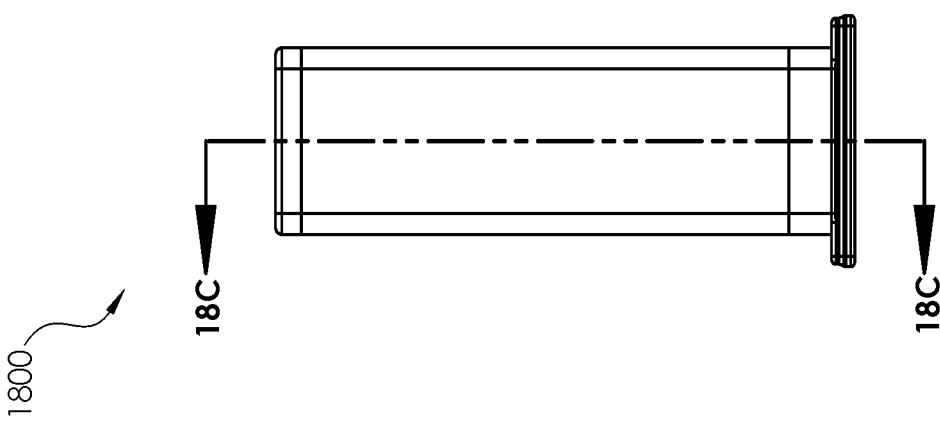
FIG. 18B illustrates a front plan view of the filter cartridge assembly of FIG. 18, according to an embodiment of the present disclosure.

FIG. 18A illustrates an exploded view of a filter cartridge assembly 1800, according to an embodiment of the present disclosure. FIG. 18B illustrates a plan view of the filter cartridge assembly 1800 in an assembled state, according to an embodiment of the present disclosure. FIG. 18C illustrates a cross-sectional view of the filter cartridge assembly 1800 in the assembled state along the line 18C-18C of FIG. 18B. In various embodiments, the filter cartridge assembly 1800 may be used as the filter cartridge assembly 1630 of FIG. 16B. In various embodiments, the filter cartridge assembly 1800 may be used in conjunction with any of the various electronic smoking device embodiments described herein. In various embodiments, any of the various filter cartridge assembly embodiments disclosed herein may be used in conjunction with any of the various electronic smoking device embodiments described herein.

The filter cartridge assembly 1800 includes an open-ended outer body 1810, which is enclosed at the top by an inlet cap 1804 and enclosed at the bottom by a vented outlet cap 1814. The inlet cap 1804 can, in various embodiments, be sealed with O-rings (such as the O-ring 1802), a quarter turn lock, a threaded seal, or simply a tight material fit within the outer body 1810, or any other appropriate sealing mechanisms, to form a leak-free seal. Between the inlet cap 1804 and the vented outlet cap 1814, and housed within the main enclosure body 1810, are various filtering mechanisms that assist in removing odors and particulate matter from emissions blown into the filter cartridge assembly 1800. Emissions are received into the filter cartridge assembly 1800 via the inlet cap 1804. Once the emissions pass through various filtering mechanisms housed within the main enclosure body 1810, clean, filtered emissions are emitted via the vented outlet cap 1814.

In the example embodiment shown in FIG. 18, emissions pass through the inlet cap 1804 into a mesh support structure 1807. The mesh support structure 1807 supports a cylindrical mesh filter 1806. In various embodiments, the mesh filter 1806 may comprise a stainless steel material, plastic, and/or polymer material. The mesh filter 1806 is also surrounded by a HEPA filter 1808. The HEPA 1808 filter is secured and sealed to the mesh filter 1806, the mesh support structure 1807, the inlet cap 1804, and/or the vented outlet cap 1814 by an adhesive 1809 that surrounds the perimeter of the HEPA filter 1808. A top end of the mesh support structure 1807, proximate the inlet cap 1804, is open to allow emissions to flow in from the inlet cap 1804. An opposite bottom end of the mesh support structure 1807 can be closed such that emissions which enter the inlet cap 1804 must pass through the mesh filter 1806 and the HEPA filter 1808. Once emissions have passed through both the mesh filter 1806 and the HEPA filter 1808, the emissions can moved past an open outlet check valve 1812 and out of the filter cartridge assembly 1800 through the vented outlet cap 1814.

FIG. 19A illustrates an exploded view of a filter cartridge assembly 1900 which is a slightly modified embodiment of the filter cartridge assembly 1800. In FIG. 19A, the HEPA filter 1808 from FIG. 18A has been replaced by a corrugated filter 1908. The corrugated filter 1908 may also be a HEPA filter, but corrugated. The corrugated shape of the corrugated filter 1908 provided additional surface area for additional filtering, while also providing more channels to provide improved airflow through the filter cartridge assembly 1800. FIG. 19B provides a plan view of the support structure 1807 and corrugated filter 1908. FIG. 19C provides a cross-sectional view of the support structure 1807 and corrugated filter 1908 taken along the line 19C-19C of FIG. 19B.

Figure 20B:
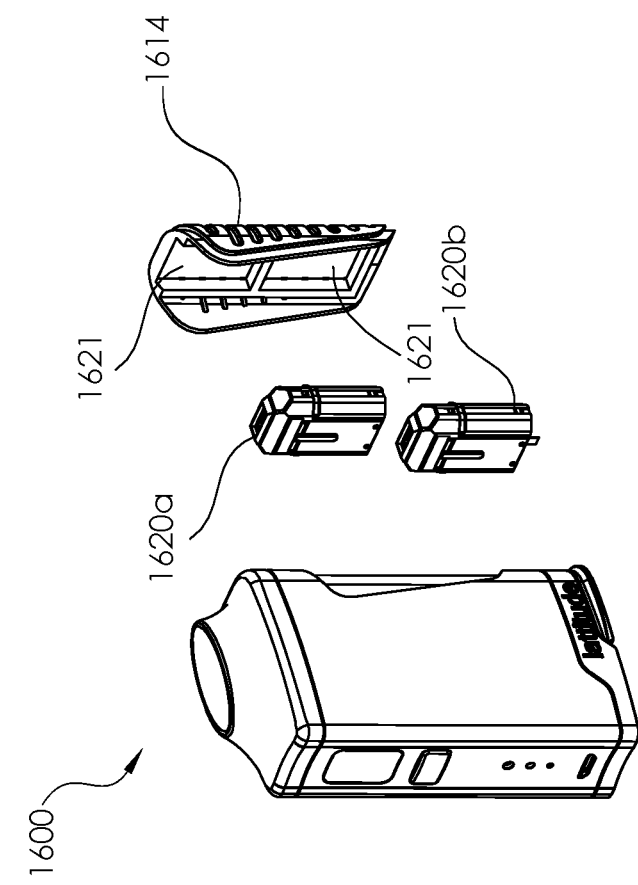
FIG. 20B illustrates a somewhat exploded view of the electronic smoking device of FIG. 20A, according to an embodiment of the present disclosure.
Figure 20A:
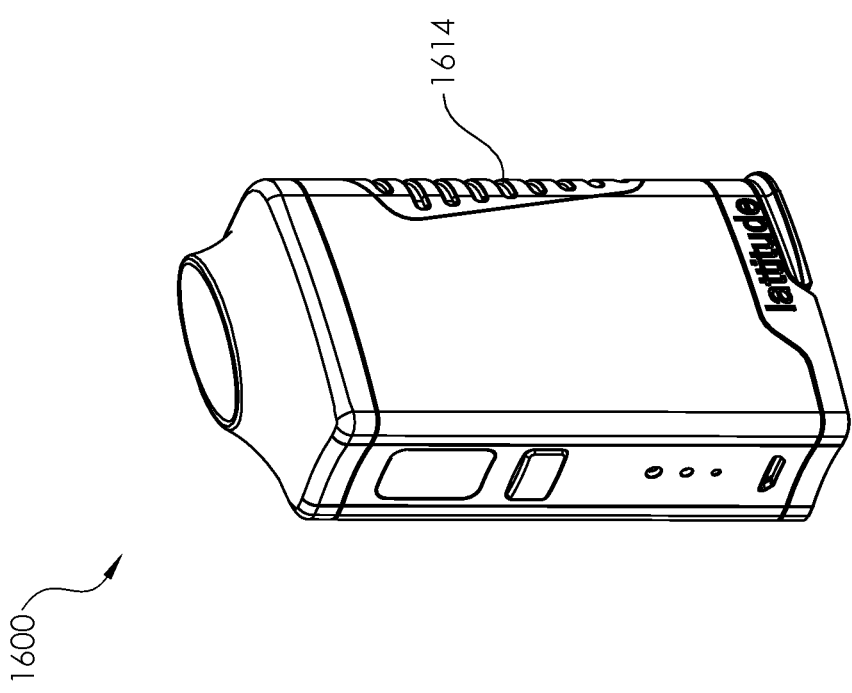
FIG. 20A illustrates a perspective view of the electronic smoking device of FIG. 16A, according to an embodiment of the present disclosure.

FIG. 20A illustrates a perspective view of the electronic smoking device 1600 of FIG. 16A. FIG. 20B illustrates a perspective view of the electronic smoking device 1600 in which the removable storage cover 1614 has been removed to reveal two compartments 1621 for storing additional vaporizer cartridge assemblies 1620a, 1620b.

Figure 21A:
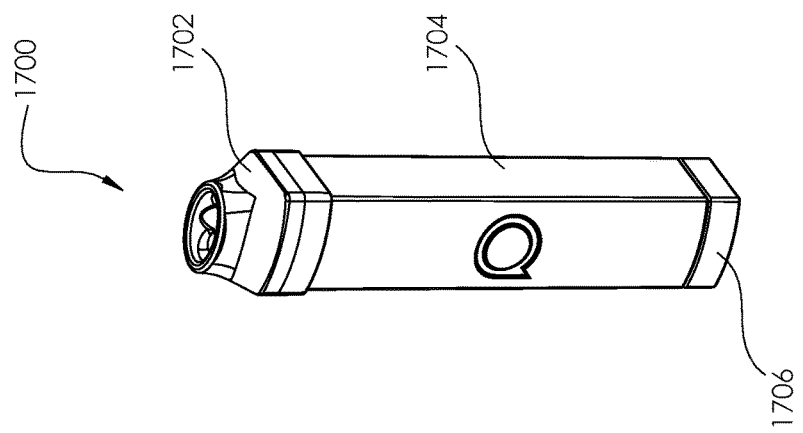
FIG. 21A illustrates a perspective view of a filter device, according to an embodiment of the present disclosure.

FIG. 21A illustrates a perspective view of an example standalone filter device 1700, in accordance with an embodiment of the present disclosure. The standalone filter device 1700 allows a user to exhale emissions into the standalone filter device 1700 to filter out odors and/or particulate matter. It should be understood that while the standalone filter device 1700 is depicted in a particular embodiment, any of the various filter assemblies and/or their various components described herein can be utilized in various combinations in alternative standalone filter device embodiments that fall within the scope of the present disclosure. The standalone filter device 1700 includes a mouthpiece 1702, an outer body (or outer enclosure) 1704, and a vented outlet cap 1706. A user can exhale into the mouthpiece 1702. The mouthpiece 1702 may have any of the characteristics of the various mouthpieces disclosed herein. For example, the mouthpiece may be removable and/or replaceable, and may be imbued with various flavors and/or scents. The user's exhaled emissions are filtered by a filter assembly comprising various filtering components housed within the outer body 1704, and the filtered air exits the standalone filter device 1700 through the vented outlet cap 1706.

Figure 21B:
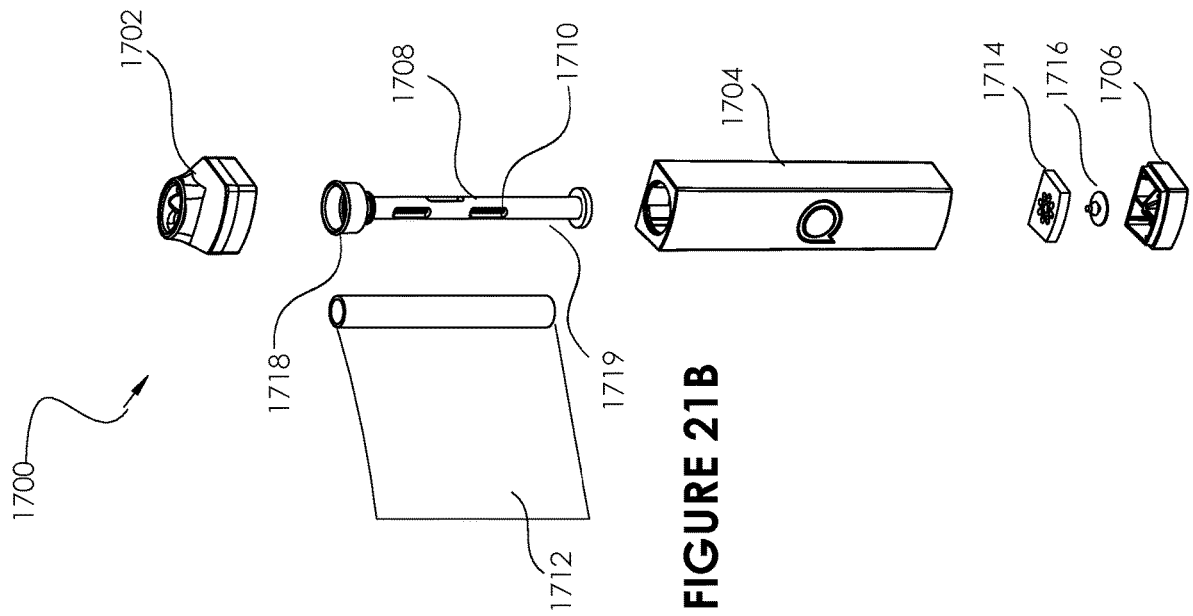
FIG. 21B illustrates an exploded view of the filter device of FIG. 21A, according to an embodiment of the present disclosure.

FIG. 21B illustrates an exploded view of the standalone filter device 1700, in accordance with an embodiment of the present disclosure. FIG. 21C illustrates a plan view of the standalone filter device 1700. FIG. 21D illustrates a cross-sectional view of the standalone filter device 1700 along the line 21D-21D of FIG. 21C, and FIG. 21E illustrates a cross-sectional view of the standalone filter device 1700 along the line 21E-21E of FIG. 21C. FIG. 21F illustrates the same cross-sectional view of the standalone filter device 1700 as that shown in FIG. 21D. FIG. 21G illustrates a close-up view of the standalone filter device 1700 defined by the area 21G of FIG. 21F.

As most clearly seen in FIG. 21B, the standalone filter device 1700 includes an open-ended, hollow outer body 1704. One end of the outer body 1704 is configured to be secured to a mouthpiece 1702, and the opposite end of the outer body 1704 is configured to be secured to a vented outlet cap 1706. Between the mouthpiece 1702 and the vented outlet cap 1706, and housed within the outer body 1704, is a filter assembly comprising various filtering mechanisms that assist in removing odors and particulate matter from emissions blown into the standalone filter device 1700. Once the emissions pass through the filter assembly housed within the main outer body 1704, clean, filtered emissions are emitted via the vented outlet cap 1706.

When a user blows emissions into the mouthpiece 1702, emissions enter a venturi core 1708. As most clearly shown in FIG. 21G, the venturi core 1708 and the outer body 1704 can be configured to form an airtight seal to ensure that emissions that have entered the standalone filter device 1700 do not leak. For example, the venturi core 1708 and the outer body 1704 may be permanently and/or semi-permanently sealed together using adhesive, or sonic welding, or any other means of airtight sealing. The venturi core 1708 includes a funneled inlet 1718 having a wider mouth portion that narrows into a stem portion 1719. The narrowing of the funneled inlet 1718 into the stem portion 1719 serves several purposes. First, the narrowing causes a thick emission cloud blown into the mouthpiece 1702 to take on a thinner, longer shape. The thinning of the emissions causes a greater portion of the emissions to come into contact with any inner wall of the venturi core 1708, thereby encouraging condensation of the emissions. Condensation of the emissions removes impurities and particulate matter from the emissions.

The narrowing of the funneled inlet 1718 into the stem portion 1719 also causes the emissions to accelerate through an inner cavity 1720 of the venturi core 1708 due to the venturi effect. The inner cavity 1720 is defined by a plurality of inner surfaces (e.g., walls) extending along substantially the length of the stem portion 1719 of the venturi core 1708, as most clearly shown in FIGS. 21D and 21E. As most clearly seen in FIG. 21D, the inner cavity 1720 is substantially enclosed except for a few openings 1710 placed around the stem portion 1719. Due to the limited openings 1710 from the inner cavity 1720, emissions that enter the inner cavity 1720 circulate around the inner cavity 1720 before they gradually exit the various openings 1710. As the emissions circulate around the inner cavity 1720, they contact the various surfaces within the inner cavity 1720. The surfaces (e.g., walls) within the stem portion 1719 provide surface area that encourages condensation of the emissions. The venturi effect and increased velocity of the emissions also causes a greater degree of convection and movement within the inner cavity 1720, which encourages greater condensation and removal of impurities. In this way, the design of the venturi core 1708 assists in keeping emissions trapped within the standalone filter device 1700 for a longer period of time, and encourages condensation of the emissions within the venturi core 1708, thereby increasing the effectiveness with which the emissions can be filtered.

The narrower stem portion 1719 of the venturi core 1708 is surrounded by a cylindrical filter 1712. The filter 1712 may be, for example, a HEPA filter made of polyester, metal, or any other appropriate material. In various embodiments, the filter 1712 may be made of any other filter material discussed herein. Emissions may exit the inner cavity 1720 via the one or more openings 1710 in the stem portion 1719, and then through the filter 1712. Emissions pass through the filter 1712 into an outer cavity 1722 defined by an area between the cylindrical filter 1712 and the outer body 1704 (FIG. 21D). In an embodiment, the outer cavity 1722 can be filled with odor-absorbing micro-pellets (e.g., carbon micro-pellets) and/or moisture absorbing micro-pellets. The emissions pass through the odor- and/or moisture-absorbing micro-pellets in the outer cavity 1722, towards a base enclosure 1714. The base enclosure 1714 includes one or more openings. The one or more openings are aligned with a one-way outlet check valve 1716. The base enclosure 1714 may be permanently and/or semi-permanently sealed with the outer body 1704. For example, the base enclosure 1714 may be permanently and/or semi-permanently sealed with the outer body 1704 using adhesives and/or sonic welding. The one-way outlet check valve 1716 prevents a user from inhaling on the mouthpiece 1702, such that a user can only exhale emissions into the standalone filter device 1700. In the depicted embodiment, when a user tries to inhale on the mouthpiece 1702, the one-way outlet check valve 1716 is pulled towards the base enclosure 1714, and covers all openings in the base enclosure 1714, to form an air-tight seal that prevents inhalation. When a user exhales into the mouthpiece 1702, the one-way outlet check valve 1716 is pushed away from the base enclosure 1714, exposing the one or more openings in the base enclosure 1714. Filtered emissions can pass through the one or more openings in the base enclosure 1714, and out of the standalone filter device 1700 via one or more openings in the vented outlet cap 1706. The vented outlet cap 1706 can also be permanently and/or semi-permanently sealed to the outer body 1704 (e.g., using adhesives, or sonic welding, or any other appropriate means).

In an embodiment, the standalone filter device 1700 may be used as a filter cartridge assembly that is inserted into an electronic smoking device, various embodiments of which have been disclosed herein. For example, as discussed above, the outer body 1704 can be permanently and/or semi-permanently sealed to the venturi core 1708, the base enclosure 1714, and the vented outlet cap 1706, such that these components, and the components contained therein (e.g., filter 1712, outlet check valve 1716, odor and/or moisture-absorbing micro-pellets), may define a closed filter cartridge assembly. The closed filter cartridge assembly can be used as a standalone-filter device by securing a mouthpiece 1702, or the mouthpiece 1702 can be removed, and the closed filter cartridge assembly can be inserted into an electronic smoking device.

Figure 21H:
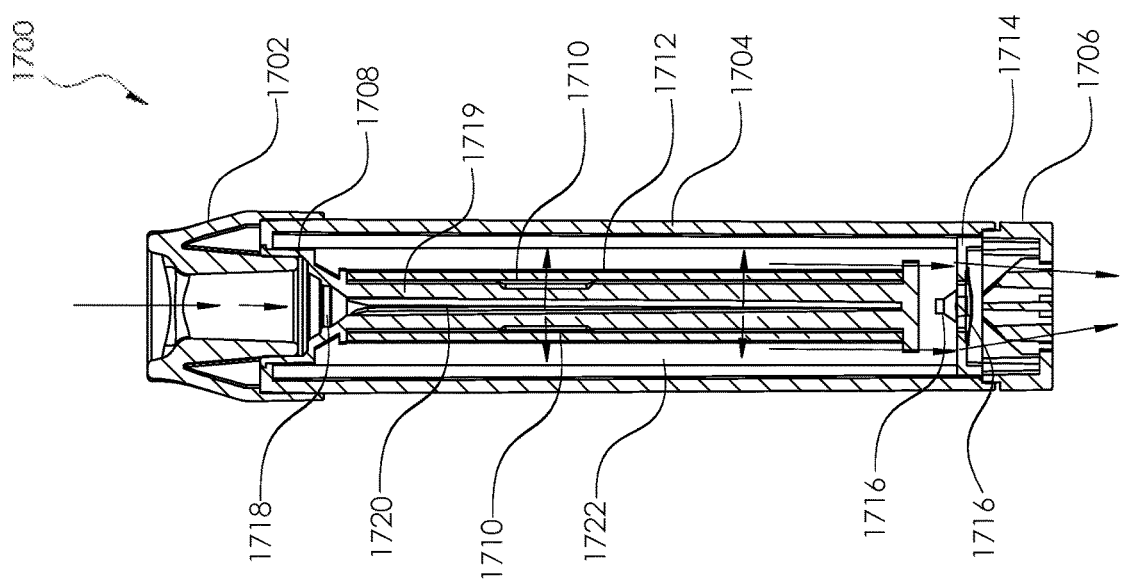
FIG. 21H illustrates the cross-sectional view of the filter device previously depicted in FIG. 21D, according to an embodiment of the present disclosure.

FIG. 21H illustrates the same cross-sectional view of the standalone filter device 1700 as is depicted in FIG. 21D. FIG. 21H includes arrows to indicate how emissions work their way through the standalone filter device 1700, as was previously described above with reference to FIGS. 21A-G. Emissions are blown into a mouthpiece 1702 of the standalone filter device 1700 and into a funneled inlet 1718 of a venturi core 1708. The funneled inlet 1718 causes the emissions to both thinner, more stretched out form, and also causes the emissions to accelerate into an inner cavity 1720 of a narrower stem portion 1719. The emissions circulate within the inner cavity 1720. A plurality of surfaces/walls surrounding the inner cavity 1720 cause the emissions to condense into condensate. As the emissions circulate within the inner cavity 1720, the emissions gradually exit the inner cavity 1720 through one or more openings 1710 in the stem portion 1719. The narrow stem portion 1719 is surrounded by a filter (e.g., a HEPA filter) 1712. As such, emissions that pass through the one or more openings 1710 pass through the filter 1712 into an outer cavity 1722. The outer cavity 1722 may, in various embodiments, be filled with odor-absorbing and/or moisture-absorbing micro-pellets. The emissions pass through the odor-absorbing and/or moisture-absorbing micro-pellets in the outer cavity 1722 towards a base enclosure 1714. The downward-moving emissions push a one-way outlet check valve 1716 away from one or more openings in the base enclosure 1714, and exit the standalone filter device 1700 through a vented outlet cap 1706.

While various embodiments of the disclosed technology have been described above, it should be understood that they have been presented by way of example only, and not of limitation. Persons skilled in the art will appreciate that various modifications can be made without departing from the invention. Likewise, the various figures may depict an example configuration for the disclosed technology, which is done to aid in understanding the features and functionality that can be included in the disclosed technology. For example, while the example electronic smoking device 100 is depicted and described in conjunction with a vaporizer portion 200 and a filter cartridge assembly 114; the electronic smoking device 1000 is depicted and described in conjunction with a vaporizer portion 1100 and a filter cartridge assembly 1014; and the electronic smoking device 1600 is depicted and described in conjunction with a vaporizer portion 1601 and a filter portion 1603, it should be understood that the various vaporizer portions and/or filtering portions and their respective components can be used interchangeably and in various combinations and used in different electronic smoking device embodiments. Similarly, while various example materials and example sizes have been disclosed, such materials and sizes are disclosed only as possible embodiments to aid in understanding and describing various features and functionality of the disclosed technology. The disclosed technology is not restricted to the illustrated example configurations, but the desired features can be implemented using a variety of alternative configurations. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention. Accordingly, the invention is defined only by the following claims.

The invention claimed is:
1. A filter device comprising:
   a mouthpiece;
   a filter assembly in communication with the mouthpiece for filtering air exhaled into the mouthpiece, the filter assembly having a venturi core comprising:
      a funneled inlet portion having a wide end directed toward the mouthpiece to receive emissions blown into the mouthpiece and a narrow end directed away from the mouthpiece, and
      a stem portion extending from the narrow end of the funneled inlet portion; and
   an outlet check valve which permits air to be exhaled through the mouthpiece into the filter assembly and substantially prohibits air from being inhaled from the filter assembly into the mouthpiece.

2. The filter device of claim 1, wherein the outlet check valve is a one-way valve which opens when a user exhales into the mouthpiece, and seals when a user inhales from the mouthpiece.

3. The filter device of claim 1, wherein the mouthpiece is removably secured to the filter assembly.

4. The filter device of claim 1, wherein the stem portion comprises one or more openings to permit emissions to exit the inner cavity.

5. The filter device of claim 1, wherein an inner surface of the stem portion defines an inner cavity, and the inner surface of the stem portion comprises a plurality of walls.

6. The filter device of claim 4, wherein
the stem portion is housed within an outer body,
an area between the stem portion and the outer body defines an outer cavity, and
the one or more openings permit emissions to exit the inner cavity into the outer cavity.

7. The filter device of claim 4, wherein the one or more openings are covered by a filter.

8. The filter device of claim 7, wherein the filter is a HEPA filter.

9. The filter device of claim 8, wherein the filter is a polyester HEPA filter.

10. The filter device of claim 6, wherein
the outer body is hollow and has a first open end opposite the second open end, and
the outer body is sealed at the first open end by the funneled inlet portion of the venturi core, and the outer body is secured at the second end to a base enclosure, and further wherein
the base enclosure comprises one or more openings, and
the outlet check valve is configured to selectively seal the one or more openings based on a direction of air flow through the filter assembly.

11. The filter device of claim 6, wherein the outer cavity houses a plurality of odor-absorbing pellets.

12. The filter device of claim 11, wherein the plurality of odor-absorbing pellets comprise a plurality of carbon pellets.

13. The filter device of claim 6, wherein the outer cavity houses a plurality of moisture-absorbing pellets.

14. The filter device of claim 10, wherein the outlet check valve is configured to be pushed away from the one or more openings in the base enclosure when a user exhales into the mouthpiece, and configured to be pulled towards the one or more openings in the base enclosure, sealing the one or more openings, when a user inhales into the mouthpiece.

* * * * *